(12) United States Patent
Pautot

(10) Patent No.: US 9,208,557 B2
(45) Date of Patent: Dec. 8, 2015

(54) SYSTEM AND PROCESS FOR ESTIMATING A QUANTITY OF INTEREST OF A DYNAMIC ARTERY/TISSUE/VEIN SYSTEM

(75) Inventor: Fabrice Pautot, La Ciotat (FR)

(73) Assignee: OLEA MEDICAL, La Ciotat (FR)

( * ) Notice: Subject to any disclaimer, the term of this patent is extended or adjusted under 35 U.S.C. 154(b) by 287 days.

(21) Appl. No.: 13/878,623

(22) PCT Filed: Oct. 11, 2011

(86) PCT No.: PCT/FR2011/052374
§ 371 (c)(1),
(2), (4) Date: Jun. 17, 2013

(87) PCT Pub. No.: WO2012/049421
PCT Pub. Date: Apr. 19, 2012

(65) Prior Publication Data
US 2013/0266201 A1    Oct. 10, 2013

(30) Foreign Application Priority Data
Oct. 11, 2010    (FR) ...................................... 10 52851

(51) Int. Cl.
| | | |
|---|---|---|
| G06T 7/00 | (2006.01) |
| G06K 9/62 | (2006.01) |
| A61B 5/02 | (2006.01) |
| A61B 5/055 | (2006.01) |
| A61B 6/00 | (2006.01) |
| G01R 33/563 | (2006.01) |
| A61B 5/026 | (2006.01) |
| G01R 33/56 | (2006.01) |

(52) U.S. Cl.
CPC ........... *G06T 7/0012* (2013.01); *A61B 5/02028* (2013.01); *A61B 5/0263* (2013.01); *A61B 5/055* (2013.01); *A61B 6/507* (2013.01); *G01R 33/56366* (2013.01); *G06K 9/6296* (2013.01); *G06T 7/0016* (2013.01); *G01R 33/5601* (2013.01); *G06T 2207/10081* (2013.01); *G06T 2207/10096* (2013.01); *G06T 2207/20076* (2013.01); *G06T 2207/30016* (2013.01); *G06T 2207/30104* (2013.01)

(58) Field of Classification Search
None
See application file for complete search history.

(56) References Cited

U.S. PATENT DOCUMENTS

| | | | | |
|---|---|---|---|---|
| 5,509,412 | A | * | 4/1996 | Bahn .............................. 600/419 |
| 7,885,442 | B2 | * | 2/2011 | Lorenz et al. ................. 382/128 |
| 2012/0136255 | A1 | * | 5/2012 | Fan et al. ....................... 600/443 |

OTHER PUBLICATIONS

Volker J. Schmid, Quantitative Analysis of Dynamic Contrast-Enhanced MR Images Based on Bayesian P-Splines, IEEE Transactions on Medical Imaging, vol. 28, No. 6, Jun. 2009, pp. 789-798.

(Continued)

*Primary Examiner* — Utpal Shah
(74) *Attorney, Agent, or Firm* — Buchanan Ingersoll & Rooney PC

(57) ABSTRACT

The invention relate to a system and a process for estimating hemodynamic parameters by applying soft probabilistic methods to perfusion imaging. Such a process also makes it possible to estimate arterial input or complementary distribution functions and therefore more generally any quantity of interest. The invention stands out in particular from the known processes in that it requires the introduction, a priori, of soft information of physiological or hemodynamic nature without constraining of forcing the desired estimation through arbitrary or undesirable hypotheses.

14 Claims, 5 Drawing Sheets

(56) References Cited

OTHER PUBLICATIONS

Erwan Gravier et al., Fully 4D motion-compensated reconstruction of cardiac SPECT images, Institute of Physics Publishing, Physics in Medicine and Biology, vol. 51, No. 18, Sep. 21, 2006, pp. 4603-4619.

Peter J. Green, Bayesian Reconstructions From Emission Tomography Data Using a Modified EM Algorithm, IEEE Transactions on Medical Imaging, vol. 9, No. 1, Mar. 1990, pp. 84-93.

Francesca Zanderigo, Nonlinear Stochastic Regularization to Characterize Tissue Residue Function in Bolus-Tracking MRI: Assessment and Comparison with SVD, Block-Circulant SVD, and Tikhonov, IEEE Transactions on Biomedical Engineering, vol. 56, No. 5, May 2009, pp. 1287-1297.

A. Benavoli, Hard-Constrained versus Soft-Constrained Parameter Estimation, IEEE Transactions on Aerospace and Electronic Systems, vol. 42, No. 4, Oct. 2006, pp. 1224-1239.

Masa-Aki Sato et al., Hierarchical Bayesian estimation for MEG inverse problem, Neuroimage, Academic Press, Orlando, Fl, vol. 23, No. 3, Nov. 1, 2004, pp. 806-826.

Guillaume Marrelec et al., Estimation of the Hemodynamic Response in Event-Related Functional MRI: Bayesian Networks as a Framework for Efficient Bayesian Modeling and Inference, IEEE Transactions on Medical Imaging, vol. 23, No. 8, Aug. 2004, pp. 959-967.

Mark W. Woolrich et al., Bayesian analysis of neuroimaging data in FSL, Neuroimage, Academic Press, Orlando FL, vol. 45, No. 1, Mar. 1, 2009, pp. S173-S186.

Steven Sourbron, Technical aspects of MR perfusion, European Journal of Radiology, vol. 76, No. 3, Apr. 3, 2010, pp. 304-313.

B. Neyran et al., Mapping Myocardial Perfusion with an Intravascular MR Contrast Agent, A Robust Estimation by a Spatially Constrained Approach, Computers in Cardiology, Sep. 2005, 32, pp. 407-410.

Peter Brunecker et al., Correcting saturation effects of the arterial input function in dynamic susceptibility contrast-enhanced MRI—a Monte Carlo simulation, Magnetic Resonance Imaging, Elsevier Science, vol. 25, No. 9, Oct. 25, 2007, pp. 1300-1311.

Mark W. Woolrich et al., Bayesian Inference of Hemodynamic Changes in Functional Arterial Spin Labeling Data, Magnetic Resonance in Medicine, vol. 56, No. 4, Oct. 1, 2006, pp. 891-906.

\* cited by examiner

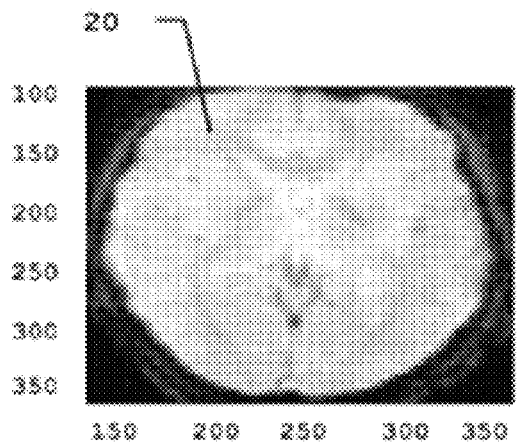
FIG. 3
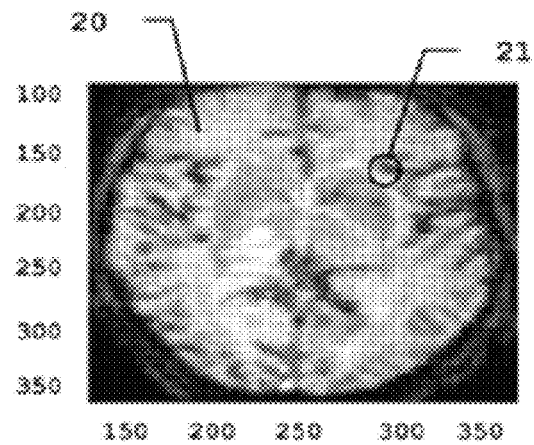
FIG. 4
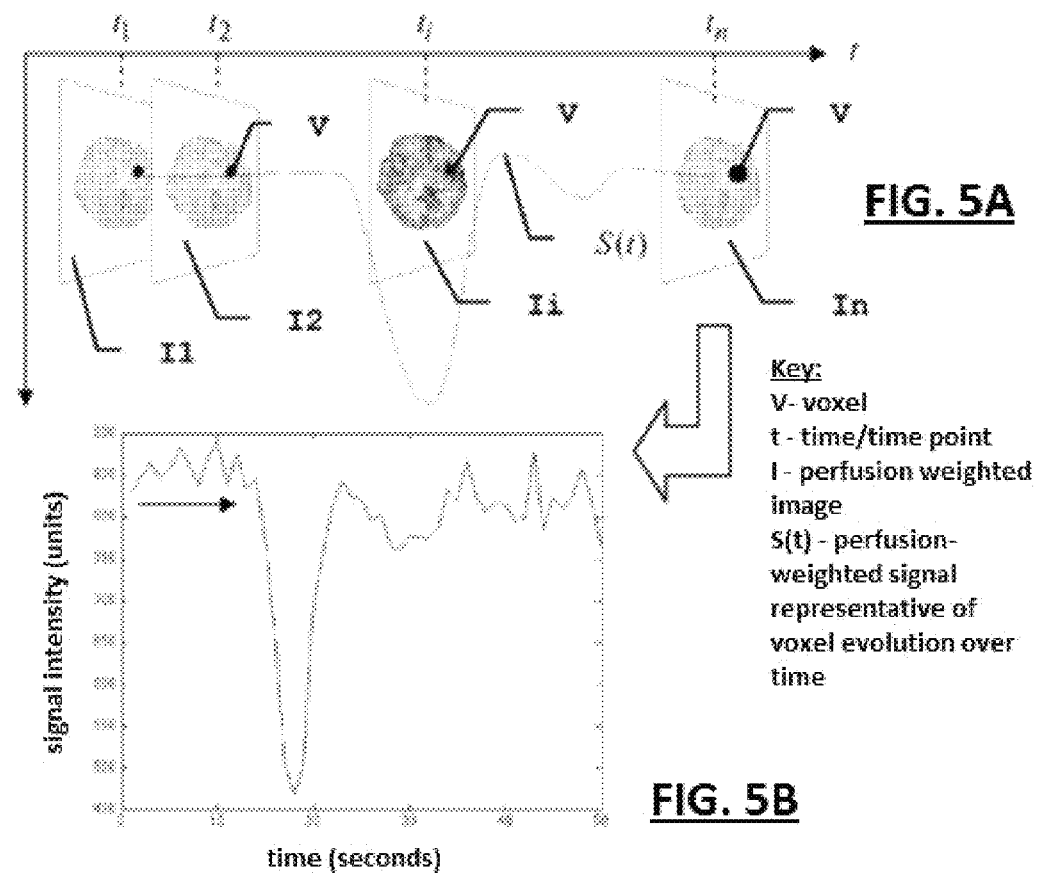
FIG. 5A
Key:
V - voxel
t - time/time point
I - perfusion weighted image
S(t) - perfusion-weighted signal representative of voxel evolution over time
FIG. 5B

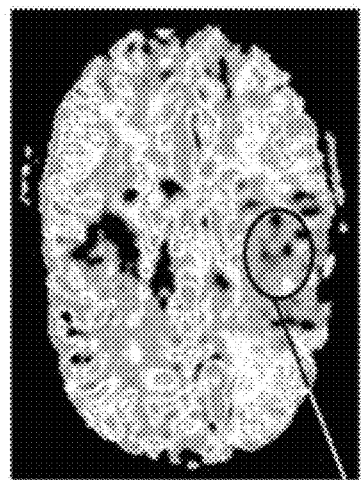
FIG. 9
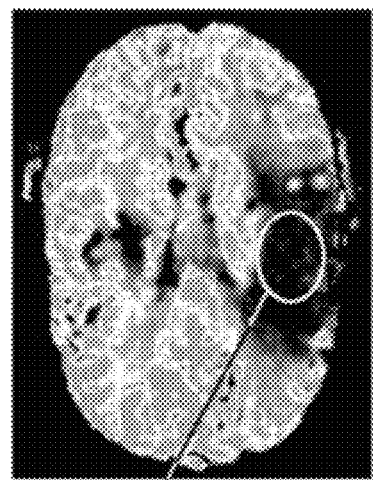
80  FIG. 10
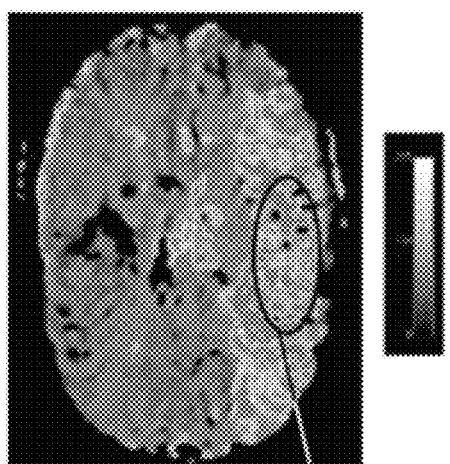
FIG. 11  81
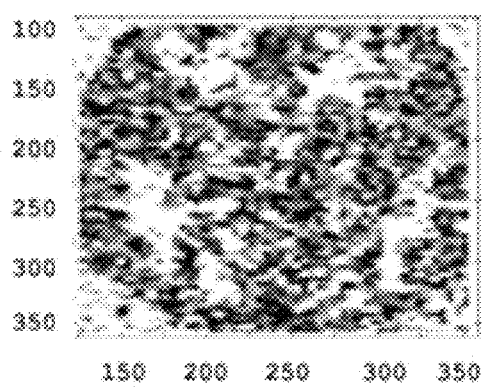
FIG. 12

SYSTEM AND PROCESS FOR ESTIMATING A QUANTITY OF INTEREST OF A DYNAMIC ARTERY/TISSUE/VEIN SYSTEM

The invention relates to a system and a method for estimating hemodynamic parameters by applying soft probabilistic methods to perfusion-weighted imaging. Moreover, such a method allows estimating complementary cumulative density functions or arterial input functions and, subsequently and more generally, any quantity of interest. The invention differs from known methods especially in that it requires introducing soft prior physiological or hemodynamic information without constraining or enforcing the required estimate by arbitrary and undesirable hypotheses.

The invention relies in particular on Perfusion-Weighted Magnetic Resonance Imaging (PW-MRI) or Perfusion Computed Tomography (CT). Those techniques allow obtaining quickly useful information on the hemodynamics of organs such as the brain or the heart. This information is particularly crucial for helping a medical practitioner to make a diagnosis and a therapeutic decision in the emergency treatment of pathologies such as brain acute stroke.

Those techniques rely on a Nuclear Magnetic Resonance or a Computed Tomography apparatus. This apparatus delivers a plurality of digital images sequences of a portion of the body, such as the brain. For this purpose, said apparatus applies a combination of high-frequency electromagnetic waves on the said portion of the body and measures the signal reemitted by certain atoms. In this way, the apparatus allows determining the chemical composition and, subsequently, the kind of biological tissue in each point (or voxel) of the imaged volume.

Images sequences are analyzed by means of a dedicated processing unit. This processing unit eventually delivers hemodynamic parameters estimates from perfusion-weighted images to a medical practitioner, by means of a suitable human-machine interface. In this way, the medical practitioner can make a diagnosis and decide which therapeutic decision is suitable.

Magnetic Resonance or Computed Tomography perfusion-weighted images are obtained by injecting a contrast agent (for example a gadolinium chelate for Magnetic Resonance Imaging) intravenously and by recording its bolus over time in each voxel of the image. For sake of conciseness, we shall omit the indices x,y,z identifying the voxels. For instance, instead of denoting $S_{x,y,z}(t)$ the signal for a voxel of coordinates x,y,z, we shall simply denote it S(t). It is understood that the operations and the computations described hereafter are generally performed for each voxel of interest, so as to eventually obtain images or maps representative of the hemodynamic parameters to be estimated.

A standard model allows linking the signals intensity S(t) measured over time t to the concentration C(t) of said contrast agent.

For example, in Perfusion Computed Tomography, the signal for each voxel is directly proportional to the concentration: $S(t)=k \cdot C(t)+S_0$. In Perfusion Imaging by Nuclear Magnetic Resonance, there exists an exponential relationship $S(t)=S_0 \cdot e^{-k \cdot TE \cdot C(t)}$. In both cases, $S_0$ represents the mean signal intensity before the arrival of the contrast agent. Regarding Nuclear Magnetic Resonance Imaging, k is a constant depending on the relationship between the paramagnetic susceptibility and the concentration of the contrast agent in the tissue and TE is the echo time. The value of constant k for each voxel being unknown, it is set to an arbitrary value for all voxels of interest. Thus, one gets relative estimates and not absolute one. This relative information nevertheless remains relevant since one is mainly interested in the relative variation of those values over space, in particular between normal and pathological tissues.

Generally speaking, we shall denote $S(t)=\Psi(C(t),\Theta_S)$ the model linking the theoretical signal S(t) to the theoretical concentration of the contrast agent C(t), $\Theta_S$ being the vector of the free parameters of said model. For instance, for perfusion-weighted imaging by Magnetic Resonance or Computed Tomography, we have $\Theta_S=(S_0)$.

The conservation of the mass of the contrast agent in the volume of tissue enclosed in each voxel at each time writes as $$\frac{dC(t)}{dt} = BF \cdot [C_a(t) - C_v(t)].$$

$C_a(t)$ is the concentration of the contrast agent in the artery feeding the volume of tissue, known as the arterial input function or AIF. BF is the blood flow in the volume of tissue and $C_v(t)$ is the concentration of the contrast agent in the vein draining the volume of tissue, known as the venous output function or VOF.

Assuming the artery/tissue/vein dynamical system to be linear and time-invariant, we have $C_v(t)=C_a(t)\otimes h(t)$ where h(t) is the system impulse response—or the probability density function of the transit time of the contrast agent in the tissue—and $\otimes$ denotes the convolution product. Then, a formal solution of the previous differential equation with initial condition C(t=0)=0 writes as $C(t)=BF \cdot C_a(t) \otimes R(t)$ where R(t) is the complementary cumulative density function or residue function defined as $$R(t) = H(t) - \int_0^t h(\tau)d\tau$$

where H is Heaviside unit step generalized function. From the impulse response and the complementary cumulative density function, another hemodynamic parameter is defined, the Mean Transit Time in the tissue or MTT:

$$MTT = \int_0^{+\infty} t \cdot h(t)dt = \int_0^{+\infty} R(t)dt \left(\text{if } \lim_{t \to +\infty} t \cdot h(t) = 0\right).$$

One can also define the blood volume BV by the relationship $BV=BF \cdot MTT$.

In perfusion-weighted imaging by nuclear magnetic resonance, hemodynamic parameters such as BF, MTT or BV as well as complementary cumulative density function are currently estimated as follows.

For each voxel, the experimental perfusion signal $S_{exp}(t)$ sampled at time points $t_i, i=1,N$, is converted into a concentration-time curve C(t) by using the relationship:

$$\forall i = 1, NC(t_i) = -\frac{1}{k \cdot TE} \ln\left[\frac{S_{exp}(t_i)}{\hat{S}_0}\right].$$

The constant k is set to a non-zero arbitrary value (e.g. $k \cdot TE=1$) for all voxels. The constant $S_0$ is estimated by taking, for instance, its mean before the arrival of the contrast agent. Let us note that this is possible only if the perfusion signals acquisition starts sufficiently early compared to the bolus arrival time of the contrast agent or BAT. From the concentration C(t), and assuming the associated theoretical arterial input function $C_a(t)$ to be known, the product BF·R(t) is estimated by numerical deconvolution.

Several approaches have been proposed in order to obtain theoretical arterial input functions $C_a(t)$ for deconvolution of the concentration-time curves C(t).

In a first approach, the medical practitioner selects a global experimental arterial input function manually. It can be measured, for instance, in the contralateral sylvian artery or in the internal carotid artery for brain perfusion imaging, or obtained from additional measurements, for instance optical ones. If it allows obtaining signals with high signal-to-noise ratios, this approach nevertheless has many drawbacks. First of all, it requires human intervention and/or additional measurements. This is undesirable in clinical emergency situation and this makes the procedures and the final results more difficult to reproduce. Second and above all, this global arterial input function does not match the local arterial input functions of each voxel. It differs from them in terms of delay (because local arterial input function are in general late compared to the global arterial input function taken upstream in the vascular system) and dispersion (because the contrast agent propagation is slower downstream to the vascular system than upstream). Now, it is known that those phenomena finally have a considerable impact on the hemodynamic parameter estimates since, by symmetry of the convolution product, those defects directly impact the estimation of the complementary cumulative density function. So, for example, one does not finally obtain an estimate of the genuine mean transit time (Alm between the local arterial input function and the local venous output function but only a mean transit time between the global arterial input function and the venous output function. In order to overcome those discrepancies, some authors have introduced new descriptive parameters such as the $$TMAX = \underset{t}{\operatorname{argmax}} R(t)$$

parameter that quantifies the delay between the global arterial input function and the local arterial input functions, even if they do not belong to the original standard perfusion model (in which the arterial input function is the genuine local arterial input function in each voxel). Other methods tend towards minimizing the influence of those discrepancies on the local arterial input functions on the estimation of the hemodynamic parameters. However, they introduce new unknowns in the global problem and only elude it.

According to a second approach, a global arterial input function is automatically obtained from perfusion-weighted images via signal processing techniques such as data clustering or Independent Component Analysis (ICA). If this approach allows avoiding human intervention, it does not solve delay and dispersion issues inherent to global arterial input functions and introduce new unknowns (e.g. it is possible to obtain venous output functions instead of arterial input functions).

According to a third approach, local arterial input functions are automatically obtained from perfusion-weighted images by means of signal processing techniques and selection criteria. For instance, one looks for the « best» function in the immediate neighborhood of the current tissular voxel where the hemodynamic parameters or the complementary cumulative density functions are to be estimated. The purpose of this third approach is to finally obtain estimates that are less biased and more accurate by overcoming, at least in some extent, delay and dispersion problems. However, nothing guarantee, a priori and a posteriori, that the local arterial input functions obtained in this way are relevant approximations of the « true local function » for the voxel of interest. For instance, this « true» function could be located outside of the neighborhood in question (if it is too small) or, on the contrary, could be confounded with another arterial input function (if it is too large). Moreover, this « best» local arterial input function is sought among « normal» arterial input functions (i.e. with a contrast agent arrival time of short/high precocity, with a large amplitude, etc.). But, the purpose is precisely to distinguish normal arterial input functions from pathological arterial input functions, for instance ischemic ones. As a consequence, even if the final results can be better than with a global approach, the uncertainties on the local arterial input functions and, a fortiori, on the hemodynamic parameters or the complementary cumulative density functions remain in a large extent.

In order to deconvolve the experimental concentration-time curve C(t) by the theoretical arterial input function $C_a t$) as obtained from the methods described above, the standard convolution model C(t)=BF·$C_a$(t) ⊗ R(t) is first discretized over time, for instance according to the approximation of the rectangle method:

$$\forall i = 1, N,$$

$$C(t_i) = BF \cdot \int_0^{\tau_i} C_a(\tau) \cdot R(t-\tau)d\tau \approx BF \cdot \Delta t \cdot \sum_{k=0}^{i} C_a(t_i) \cdot R(t_i - t_k)$$

where Δt the sampling period. In this way, we come down to a linear system Ad=c if we let $$A = \Delta t \cdot \begin{pmatrix} C_a(t_1) & 0 & \cdots & 0 \\ C_a(t_2) & C_a(t_1) & \ddots & \vdots \\ \vdots & \vdots & \ddots & 0 \\ C_a(t_N) & C_a(t_{N-1}) & \cdots & C_a(t_1) \end{pmatrix}$$

$$b = \begin{vmatrix} R(t_1) \\ R(t_2) \\ \cdots \\ R(t_N) \end{vmatrix}$$

$$c = \begin{vmatrix} C(t_1) \\ C(t_2) \\ \cdots \\ C(t_N) \end{vmatrix}$$

$$d = BF \cdot b$$

In practice, matrix A is severely ill conditioned and almost singular, so that one cannot numerically solve the linear system without obtaining meaningless solutions and aberrant estimates. Therefore, one has to resort to various methods in order to obtain, for example, a pseudo-inverse $Ã^{-1}$ of matrix A and, subsequently, an estimate d̂ of d by d̂=$Ã^{-1}$·c. Those methods for obtaining a pseudo-inverse, include Truncated Singular Value Decomposition (T)SVD), Simple Singular Value Decomposition (sSVD), and Hunt deconvolution in the frequency domain.

More generally, one can minimize a criterion such as $\|Ad-c\|^2 + \|\Gamma d\|^2$ where $\|\delta d\|^2$ is a regularization term that favors certain solutions and allows obtaining an estimate of d by $$\hat{d} = \underset{d}{\mathrm{argmin}}(\|Ad - c\|^2 + \|\Gamma d\|^2).$$

Those methods include Tikhonov regularization and wavelet transform-based methods, etc.

Once $\hat{d}$ is obtained, one can obtain an estimate $\widehat{BF}$ of BF by $\widehat{BF} = \hat{d}(t_1) = \hat{d}(0)$ ince, by definition, $$\lim_{t \to 0^+} R(t) = 1.$$

However, BF is often estimated as $$\widehat{BF} = \max_{i=1}^{N} \hat{d}(t_i),$$

for instance within singular value decomposition-based methods, in order to compensate for the systematic underestimation of $\hat{d}(0)$ inherent to those methods. Subsequently, one obtains an estimate $\hat{b}$ of b by $$\hat{b} = \frac{\hat{d}}{\widehat{BF}}$$

and an estimated of $$MTT = \int_0^{+\infty} R(t) dt \text{ by } \widehat{MTT}^{Q^-} = \Delta t \cdot \sum_{i=2}^{N} t_i \cdot \hat{h}^Q(t_i)$$

by following, for example, the rectangle method approximation. Last, one typically obtains an estimate of BV by $\widehat{BV} = \widehat{BF} \cdot \widehat{MTT}$ even if the estimator of a product is not the product of the estimators.

One can find many variations on those arterial input function(s)-based methods: for example, the experimental arterial input functions can be first fitted to a parametric or semi-parametric theoretical model $C_a(t, \Theta_a)$ where $\Theta_a$ is a vector of parameters, in order to artificially increase the signal-to-noise ratio. As well, the signal can be artificially oversampled in order to make the numerical deconvolution more stable or to overcome potential problems arising from recirculation, when there is time overlapping between the contrast agent circulation signal (first pass) and the recirculation signal (second pass). But those variations are still based on numerical deconvolution methods such as truncated singular value decomposition.

According to certain comparative studies, among the different methods that have been benchmarked on synthetic data meant to simulate typical real data, singular value decomposition-based deconvolution and its variations (linear truncated singular value decomposition (sSVD), truncated circular (cSVD) or smoothed truncated circular (oSVD)) finally yield the best estimates of the BF and MTT parameters in terms of bias (systematic error with respect to the true value), precision (standard deviation of the estimate with respect to the true value as a function of the signal-to-noise ratio of the input signals) and robustness with respect to the various complementary cumulative density functions R(t) and arterial input functions $C_a(t)$ that can occur in practice, depending on the patients, the kind of tissue, the pathologies, etc.

However, on the top of the problems related to the selection of the arterial input functions described above, this family of numerical methods suffers drastic inherent issues.

First of all, the estimates $\hat{d}$ of BF.b are not decreasing over time but oscillating, in such an extent that they can sometimes take negative values. But R(t), which is the amount of contrast agent remaining in the voxel at time t, is necessarily a positive and decreasing function. Ad hoc methods such as oSVD allow reducing those aberrant oscillations but they remain since they are inherent to singular value decomposition. This is the reason why, within this family of methods, one estimates the blood flows BF by $$\widehat{BF} = \max_{i=1}^{N} \hat{d}(t_i)$$

whereas they should instead be estimated as $$\widehat{BF} = \hat{d}(0) \text{ since } \lim_{t \to 0^+} R(t) = 1$$

within the standard perfusion model. By taking the maximum instead of the value at the origin, one only hopes to erase the effect of those oscillations on the BF estimate. Hence, those methods cannot be perfectly satisfactory. In particular, the accuracy of the BF estimates that can be reached by more rigorous estimation methods of the complementary cumulative density functions and, subsequently, of the hemodynamic parameters remains unknown. So, those numerical deconvolution methods contradict the standard perfusion model since they provide solutions that do not fulfill the properties of said model.

In order to get rid of this problem and to obtain physiologically admissible estimates of the complementary cumulative density functions, parametric models $R(t, \Theta_R)$ for those complementary cumulative density functions have been introduced, $\Theta_R$ being the vector of the parameters of said model. These models are fitted to experimental signals, for instance by using Bayes method. However, this approach seems to be premature at this point. Indeed, one should have at one's disposal prior nonparametric estimates of the complementary cumulative density functions in order to determine parametric or semi-parametric models suitable to describe them because Monte-Carlo simulations have shown that if those models are not perfectly suitable to correctly describe all kinds of complementary cumulative density functions that can occur in practice, then the resulting estimates of hemodynamic parameters such as MTT or BF become aberrant. Hence, the choice of theoretical models for the complementary cumulative density functions is critical and can be properly made only by applying the models to experimental data. Hence the necessity of nonparametric methods to estimate said complementary cumulative density functions, in order to possibly replace them in a next step by classical parametric or semi-parametric methods allowing to get physiologically admissible estimates of the complementary cumulative density functions.

As mentioned before, estimates obtained by deconvolution methods such as singular value decomposition contradict the very definition of $$R(t) = H(t) - \int_0^t h(\tau)d\tau$$

under the standard perfusion model.

They are not physiologically and physically admissible. It is therefore not possible to fit parametric or semi-parametric theoretical models to those estimates. A fortiori, it is not possible to compare several models each other and to select those that are the most suitable for describing the experimental cumulative density functions. Hence, it is no longer possible to make progress in the modeling and the understanding of perfusion phenomena because of defects that are inherent to numerical methods such as singular value decomposition.

Besides, it appears that the problem underlying the non-parametric estimation of complementary cumulative density functions and hemodynamic parameters is not a <<simple>> deconvolution problem of the empirical concentration-time curves by empirical arterial input functions. Indeed, it could be the case if the arterial input functions were actually given within the problem, known with absolute certainty and infinite accuracy. But one is provided at best only with experimental, measured arterial signals that are known only up to the measurement noise and that have to be pre-converted into concentration-time curves. In other words, by assuming the empirical, measured arterial input functions to be equal to the theoretical arterial input functions, one neglects the measurement noise on the experimental signals and the uncertainties coming from the estimation or the conversion of the concentration-time curves from those signals.

The standard convolution model $C(t)=BF \cdot C_a(t) \otimes R(t)$ involves only theoretical signals that cannot be directly measured in general. In fact, measured signals are the sum of theoretical signals and measurement noise. So, experimental arterial and tissular perfusion signals write respectively as $S_{exp}(t)=S_{th}(t)+\xi_t$ and $S_{a_{exp}}(t)=S_{a_{th}}(t)+\xi_t^a$ where $\xi_t$ and $\xi_t^a$ are zero-mean stochastic processes modeling the measurement noises. Moreover, we have $S_{th}(t)=S_0 e^{-C_{th}(t)}$ and $S_{ath}(t)=S_0 e^{-C_{ath}(t)}$ within magnetic resonance perfusion-weighted imaging or, more generally, $S_{th}(t)=\Psi(C_{th}(t), \Theta_S)$ as described before. Therefore, the theoretical standard perfusion model applied to experimental signals has to be written as $C_{th}(t)=BF \cdot C_{ath}(t) \otimes R(t)$ that is, within nuclear magnetic resonance perfusion-weighted imaging as:

$$\ln \frac{S_{exp}(t) - \xi_t}{S_0} = BF \cdot \ln \frac{S_{aexp}(t) - \xi_t^a}{S_{0a}} \otimes R(t)$$

or equivalently as:

$$\ln \frac{S_{exp}(t) + \xi_t}{S_0} = BF \cdot \ln \frac{S_{aexp}(t) + \xi_t^a}{S_{0a}} \otimes R(t)$$

not as:

$$C_{exp}(t)=CBF \cdot [C_{a_{exp}}(t)] \otimes R(t) + \xi_t$$

which is the erroneous implicit mathematical convolution model on which most of the deconvolution methods are based. One can see at this point that it is preferable to write the standard perfusion model as:

$$\begin{cases} S_{exp}(t) = S_0 e^{-C_{th}(t)} + \xi_t \\ S_{aexp}(t) = S_{0a} e^{-C_{ath}(t)} + \xi_t^a \\ C_{th}(t) = BF \cdot C_{ath}(t) \otimes R(t) \end{cases}$$

in order to avoid taking the logarithm of non-necessarily positive random variables.

It is known that the measurement uncertainties on the signal to be deconvolved have a considerable influence on the final result of the deconvolution process: an infinitesimal variation on the input signal due to those uncertainties can yield a considerable variation on the final result. It is precisely to overcome those issues and to reduce those instabilities that deconvolution methods such as Tikhonov regularization or singular value decomposition have been introduced. A fortiori, the influence of the measurement noises and uncertainties on the arterial input functions, that is currently entirely neglected, is even more considerable: the arterial measurement noise $\xi_t^a$ and the uncertainties on $S_{0a}$ now occur in the convolution matrix A and, as a consequence, are amplified and propagated. Neglecting the errors and the uncertainties on the arterial input functions cause important errors on the hemodynamic parameter estimates, as well as an illusion of accuracy on those estimates. Certain methods aim to erasing the measurement noises on the arterial input functions in order to minimize this problem that remains eluded up to now. It would be preferable to have at one's disposal methods allowing to propagate the uncertainties on the arterial input functions on the estimation of hemodynamic parameters and complementary cumulative density functions in order to master and to quantify estimation errors.

Besides, it would be also preferable to avoid writing the standard perfusion model as $C_{th}(t)=BF \cdot C_{ath}(t) \otimes R(t)$. Indeed, the standard perfusion model first defines the impulse response h(t) of the artery/tissue/vein dynamical system, from which the complementary cumulative density function R(t) is computed as $$R(t) = H(t) - \int_0^t h(\tau)d\tau.$$

Hence, it is convenient to write the standard perfusion model as a function of the impulse response h(t), as $$C_{th}(t) = BF \cdot C_{ath}(t) \otimes \left[ H(t) - \int_0^t h(\tau)d\tau \right],$$

to fit this model to estimate the impulse response h(t) at measurement time points $t_j, j=1,N$ by $\hat{h}$ in order to finally obtain an estimate $\hat{R}$ of the complementary cumulative density function, for example $$\hat{R}(t_j) = \left[ H(t_j) - \Delta t \cdot \sum_{i=2}^{j} \hat{h}(t_i) \right]$$

(approximation by the rectangle method). In particular, it is better not to estimate the impulse response h(t) from the estimate $\hat{R}$ of the complementary cumulative density function. From the numerical point of view, it is easy to understand that it is preferable to first estimate the derivative (h(t)) in order to estimate the antiderivative (R(t)) in a second step instead of the converse. Nevertheless, one can check that the complementary cumulative density function R(t) is estimated directly instead of the impulse response h(t).

Besides, the deconvolution problem is ill posed and admits infinitely many possible solutions. A fortiori, the ill posed problem that one faces within perfusion-weighted imaging for estimating hemodynamic parameters, impulse responses, complementary cumulative density functions or arterial input functions, is a deconvolution problem tripled with a problem of measurement noises propagation and a problem of experimental signals to concentration-time curves conversion.

In order to come down to a well-posed problem possibly admitting a unique solution, one has to add prior information, constraints on the solution sought among the infinity of a priori possible solutions. This is the reason why, one can find many deconvolution and estimation methods in the state-of-the-art, each method injecting, more or less explicitly, or more or less directly, a particular kind of prior information.

As an example, we can mention classical Tikhonov regularization, as described before. In its most popular version, matrix $\Gamma$ is equal to $\Gamma = \alpha I_N$. This penalizes the solutions of large Euclidean norm, the scalar $\alpha$ quantifying the weight of this penalization, of this constraint.

On the other hand, truncated singular value decomposition, which is classical within perfusion-weighted imaging, consist in cancelling the singular values of the convolution matrix that are below a given threshold that plays the role of a regularization parameter. Those small singular values are related to the high-frequency components of the signal, so that the Truncated Singular value Decomposition acts as a low-pass filter. If complementary cumulative density functions are low-frequency signals, the truncation of small singular values does not directly and only correspond to additional physiological information but above all to additional algebraic information, namely the membership of a given linear subspace. One can check that too high frequency oscillations remain. The estimated signals have a tendency to follow the measurement noises (overfitting). Moreover, the truncation threshold does not amount to the weight of an explicit constraint (but only to forcing the solutions to belong to some subspace), it is difficult to give criteria to determine its value. Conversely, it is not guaranteed that one can properly optimize such a criterion, for instance the roughness of the complementary cumulative density function within the oSVD method, by truncated singular value decomposition because the action of said method on the criterion is very indirect.

In addition, current hemodynamic parameters or complementary cumulative density functions estimation methods do not allow estimating the precision of those estimates (i.e. the standard deviation of the estimator) nor the confidence that one can have in those estimates and the estimates of the precision of those estimates. In particular, it is difficult to quantify the goodness-of-fit of the standard perfusion model by deconvolution and estimation methods. So, one can note that singular value decomposition-based methods have for instance, a tendency to overfit the experimental signals. The estimated signals are not smooth but, on the contrary, have a tendency to follow the measurement noise. One can obtain low values for measures of the models goodness-of-fit ($\chi^2$ statistics Sum of Squared Errors), such low values are thus and misleading and $\chi^2$ statistics should be avoided if one wants to detect and to take overfitting into account. It is therefore not obvious to introduce <<good>> measures of the goodness-of-fit for the deconvolution and hemodynamic parameter estimation methods according to the state-of-the-art. It is therefore desirable to have at one's disposal methods for which such a goodness-of-fit measure is uniquely defined, allows taking overfitting into account and quantifying only the goodness-of-fit of the standard perfusion model to the data.

In summary, current methods for estimating hemodynamic parameters, impulse responses or complementary cumulative density functions are subject to many methodological flaws and many approximations that are not under control. The interpretation of the results is thus made difficult and perfusion-weighted imaging is not fully exploited.

The purpose of the present invention is to provide an answer to all the drawbacks arising from the use of known methods. The main purpose of the invention is to provide new methods allowing to seek the estimate $\hat{h}$ of the impulse response h among the solutions fulfilling certain constraints of the physiological or hemodynamical kind, without introducing ad hoc constraints that are not necessarily fulfilled and, above all, that are impossible to verify experimentally or are of a non physiological or non hemodynamical kind. Moreover, those methods allow determining the weights of such constraints in an automatic and unique way, without having to resort to ad hoc methods.

The invention thus permits claiming that the problem of estimating hemodynamic parameters, complementary cumulative density function or arterial input functions is finally well posed. The invention provides its unique solution (possibly multiple).

Among the main advantages provided by the invention, we can cite, without limitation, the fact that we can:
 translate in a quantitative way qualitative or semi-qualitative soft physiological information on the hemodynamic parameters, the impulse responses, the complementary cumulative density functions or the arterial input functions;
 explicitly take the uncertainties and the errors on the arterial input functions and the experimental signals into account and propagate them on the estimates of the quantities of interest;
 improve the estimation of those parameters, the impulse responses, the complementary cumulative density functions or the arterial input functions in terms of bias (systematic error), precision (statistical error), and robustness with respect to the different situations that can occur in practice;
 obtain confidence intervals—and even bets on said confidence intervals—on the hemodynamic parameters estimates, impulse responses, complementary cumulative density functions or arterial input functions, in order to improve and to clarify the confidence that one can have in those estimates;
 obtain nonparametric estimates of impulse responses, complementary cumulative density functions or arterial input functions that are admissible from the physiological and the hemodynamical point of view and that are compliant with the standard perfusion model, in order to allow, in a next step, the fitting, the comparison and ultimately the selection of parametric or semi-parametric theoretical models for said impulse responses, said complementary cumulative density functions or said arterial input functions;
 quantify in what extent the arterial input functions can actually be admissible arterial input functions for the tissue in each voxel of interest;

provide objective and quantitative measures of the goodness-of-fit of a global perfusion model, allowing finally to compare and to select the most suitable global perfusion models.

For this aim, the invention embodies a method for estimating a quantity of interest among a plurality of an artery/tissue/vein dynamical system in an elementary volume—referred to as a voxel—of an organ. Such a method is aimed to being carried out by a processing unit of a perfusion-weighted imaging analysis system and comprises a step for estimating the said quantity of interest from experimental perfusion data. Said step for estimating according to the invention consists in evaluating, according to Bayes method, a marginal posterior distribution for said quantity of interest by:
- assigning a direct probability distribution for the perfusion data given the parameters involved in the problem related to the estimation of the quantities of interest of the artery/tissue/vein dynamical system in question;
- assigning a joint prior probability distribution for said quantities, by introducing soft information related to the impulse response of said dynamical system.

The invention also embodies a method for estimating a quantity of interest among a plurality of an artery/tissue/vein dynamical system in an elementary volume—referred to as a voxel—of an organ, said dynamical system being linear, time-invariant and formally determined by the relationship $C(t)=BF \cdot C_a(t) \otimes R(t)$ where $C(t)$ is the concentration of a contrast agent circulating in a voxel, $C_a(t)$ is the concentration of said contrast agent in the artery feeding said voxel, BF is the blood flow in said voxel, $\otimes$ stands for the convolution product and $R(t)$ is the complementary cumulative density function of the transit time in said voxel. Such a method is carried out by a processing unit of a perfusion-weighted imaging analysis system, and comprises a step for estimating said quantity of interest from experimental perfusion data. According to the invention said estimation step consists in evaluating, according to a Bayesian method, marginal posterior distribution for said quantity of interest by:
- assigning a direct probability distribution for the perfusion data given the parameters involved in the problem related to the estimation of the quantities of interest of the artery/tissue/vein dynamical system in the voxel in question;
- assigning a joint prior probability distribution for said quantities, by introducing soft information related to the complementary cumulative density function $R(t)$ in said voxel.

According to a preferred embodiment, in both cases the invention further plans the assignment of a joint prior probability distribution for said quantities by introducing soft information related to said contrast agent concentration-time curve in the artery feeding the voxel.

The invention plans such methods may be carried out by successive iterations for a plurality of voxels in question.

According to some embodiments, a method according to the invention may comprise:
- a step for computing supplementary information represented by a confidence interval associated with an estimated quantity of interest;
- a step for computing supplementary information represented by betting odds on a confidence interval associated with an estimated quantity of interest;
- a step for computing supplementary information represented by a measure of the adequacy of the product of: the assignment of the direct probability distribution for the experimental perfusion data given the parameters involved in the problem of estimating the quantities of interest of the artery/tissue/vein dynamical system in a voxel the in question;
- the assignment of the joint prior probability distribution for said quantities.

The invention plans such methods according may comprise a step for delivering an estimated quantity of interest indeed any supplementary information associated with said estimated quantity of interest to a human-machine interface capable of rendering it to a user.

The invention also relates to—according to a second purpose—a processing unit comprising means for storing, means for communicating with the external world and means for processing. The means for communicating are capable of receiving from the external world experimental perfusion data and the means processing are adapted to carried out a process for estimating a quantity of interest according to the invention.

The means for communicating of such a processing unit may deliver—according to a preferred embodiment—
- an estimated quantity of interest in a format suitable for a human-machine interface capable of rendering it to a user.

The invention further plans a perfusion-weighted imaging analysis system comprising a processing unit according to the invention and a human-machine interface capable of rendering to a user a quantity also estimated according to a method also compliant with the invention.

Other features and advantages shall appear more clearly on reading the following description and review of the accompanying figures including:

FIGS. 3 and 4 show respectively a perfusion image, obtained by a Nuclear Magnetic Resonance imaging apparatus, of a slice of a human brain before the injection of a contrast agent and during the circulation of said contrast agent in said brain tissue;

FIGS. 5a and 5b show a perfusion-weighted signal S(t) by Nuclear Magnetic Resonance related to a voxel of a human brain;

FIG. 9 shows a map of cerebral blood volumes estimated according to the invention;

FIG. 10 shows a map of cerebral blood flows—in a case of brain ischemia—estimated according to the invention;

FIG. 11 shows a map of mean transit times estimated according to the invention;

FIG. 12 shows a map of the probability that a cerebral blood flow belongs to a confidence interval.

Figure 1:
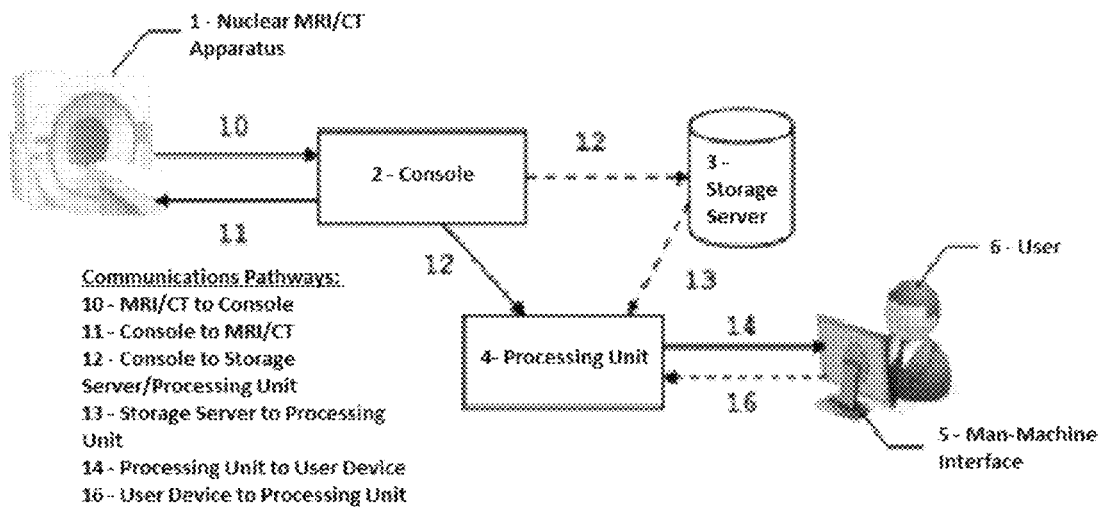
FIGS. 1 and 2 show two embodiments of a system for analyzing perfusion-weighted images.

FIG. 1 illustrates a system for analyzing perfusion-weighted images. A nuclear magnetic resonance imaging or computed tomography apparatus 1 is controlled by means of a console 2. A user can select parameters 11 to control the device 1. From information generated by the apparatus 1, one obtains a plurality of sequences of digital images 12 of a portion of a body of a human or animal. As a favorite example, we will illustrate the solutions from the prior art and the invention using digital images from the observation of a human brain. Other organs may also be considered.

The images sequences 12 may optionally be stored in a server 3 and constitute a medical record 13 of a patient. Such a record 13 may include various types of images, such as perfusion-weighted or diffusion-weighted images. Images sequences 12 are analyzed using a dedicated processing unit 4. Said processing unit comprises means for communicating with the external world to collect images. Said means for communicating further allow the processing unit to provide in fine a medical practitioner 6 or a researcher with an estimate of hemodynamic parameters 14 from perfusion-weighted images 12, by means of a dedicated human-machine interface 5. The analysis system user 6 can confirm or reject a diagnosis, make a decision on a therapeutic action that he seems appropriate, conduct further investigations . . . . Optionally, the user can configure the operation of the processing unit 4 through settings 16. For example, it can define display thresholds or select the estimated parameters he wants to view.

Figure 2:
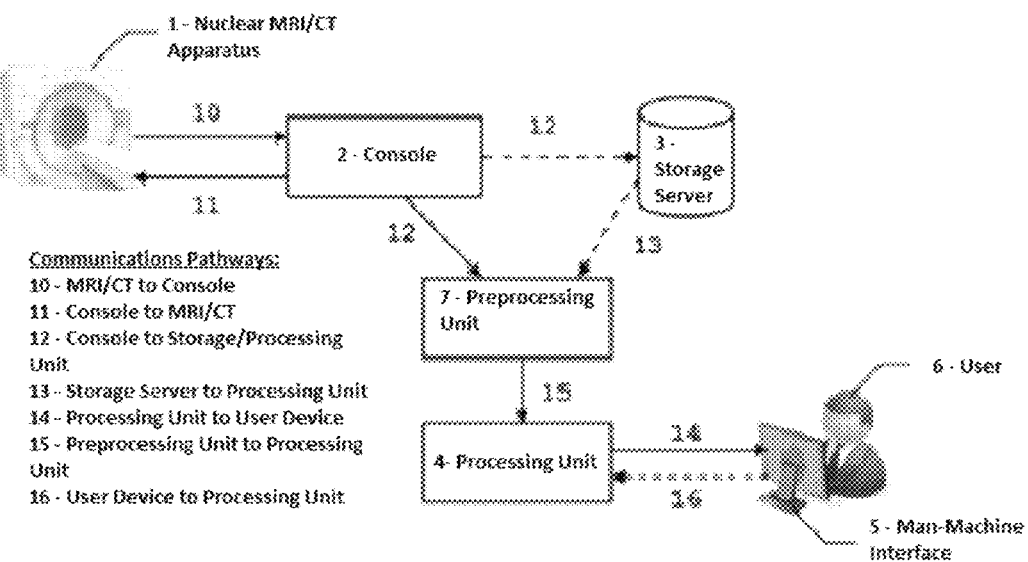

FIG. 2 illustrates an embodiment of an analysis system for which a preprocessing unit 7 analyzes images sequences 12 to retrieve perfusion data 15 for each voxel. The processing unit 4 in charge of estimating hemodynamic parameters 14 is thus relieved of this action and implements an estimation method from perfusion data 15 received by its means for communicating with the external world.

FIG. 3 shows a typical example of an image 12 of a slice of 5 mm thickness of a human brain. This image is obtained by Nuclear Magnetic Resonance. Using this technique, one can obtain, for each slice, a matrix of 128×128 voxels whose dimensions are 1.5×1.5×5 mm. Using bilinear interpolation one can produce a flat image of 458×458 pixels such as image 20.

FIG. 4 shows an image 20 similar to that shown in connection with FIG. 3. However this image is obtained after an injection of a contrast agent. This image is a typical example of a perfusion-weighted brain image. Arteries appear clearly contrary to the same image described in FIG. 3. According to known techniques, it is possible to select one or several arterial input functions 21 in the hemisphere contralateral to the pathological hemisphere in order to estimate hemodynamic parameters.

FIG. 5b illustrates an example of a perfusion-weighted signal S(t) by Nuclear Magnetic Resonance as the data 15 delivered by the preprocessing unit 7 described in connection with FIG. 2. The perfusion-weighted signal is therefore representative of the evolution of a voxel over time t following the injection of a contrast agent. For example, FIG. 5b describes such a signal over a period of 50 seconds. The ordinate describes the intensity of the signal in arbitrary units. To obtain such a signal, the processing unit 4 according to FIG. 1 (or alternatively the preprocessing unit 7 according to FIG. 2) analyses a sequence of n perfusion-weighted images by nuclear magnetic resonance $I_1, I_2, \ldots, I_i, \ldots, I_n$ at time points $t_1, t_2, \ldots, t_i, \ldots, t_n$, as described, for example, in FIG. 5a. For a given voxel, for example voxel V, one determines a perfusion-weighted signal S(t) representative of the voxel evolution over time t following an injection of a contrast agent.

Figure 6:
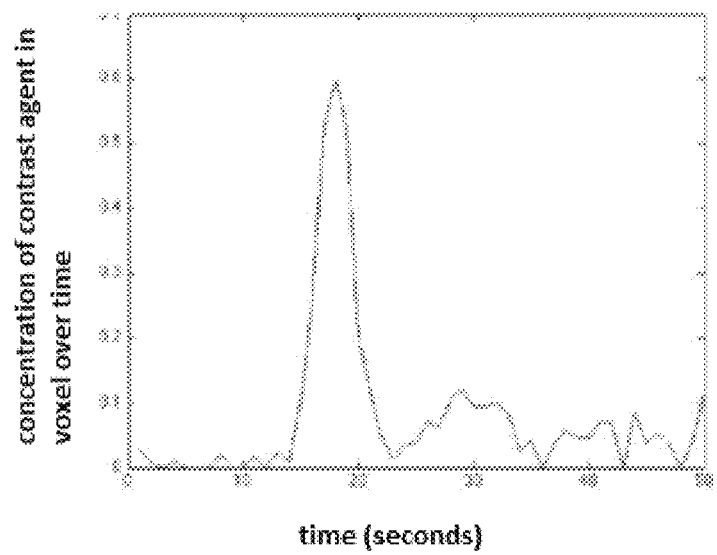
FIG. 6 shows a typical concentration-time curve C(t) of a contrast agent circulating in a voxel of a human brain.

FIG. 6 shows a concentration-time curve derived from a perfusion-weighted signal as described in FIG. 5b. As already mentioned above, there exists a relationship between a perfusion-weighted signal and an associated concentration-time curve. So, in perfusion-weighted imaging by Nuclear Magnetic Resonance, there exists an exponential relationship $S(t)=S_0 \cdot e^{-k \cdot TE \cdot C(t)}$ where $S_0$ is the average intensity of the signal before the arrival of the contrast agent, TE is the echo time and k is a constant depending on the relationship between the paramagnetic susceptibility and the concentration of the contrast agent in the tissue.

FIG. 6 allows viewing the evolution of the concentration of a contrast agent in a voxel over time. We observe that there is a high amplitude peak in the first pass of the contrast agent in the voxel followed by lower amplitude peaks related to the phenomenon of recirculation of the contrast agent (second pass).

Figure 7:
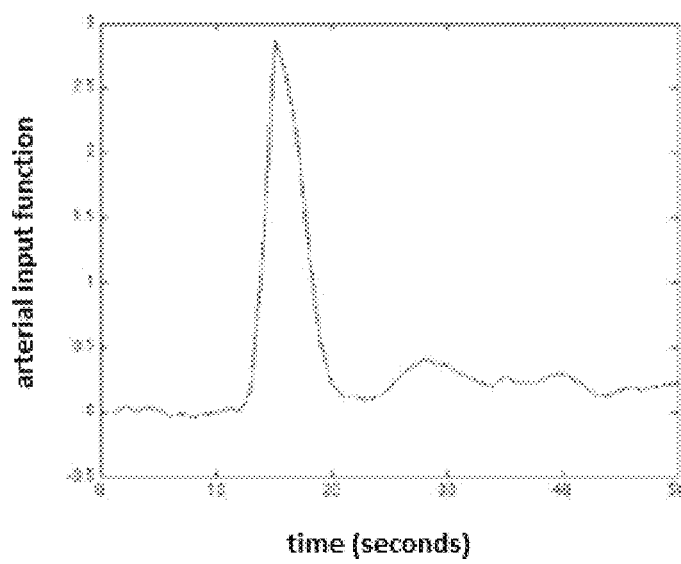
FIG. 7 shows a typical arterial input function $C_a(t)$.

FIG. 7 illustrates a typical arterial input function $C_a(t)$ representing the circulation of a contrast agent within an arterial voxel such as voxel presented in connection with FIG. 4. FIG. 7 shows in particular that the phenomenon of recirculation after the first pass of the contrast agent is very weak.

Figure 8:
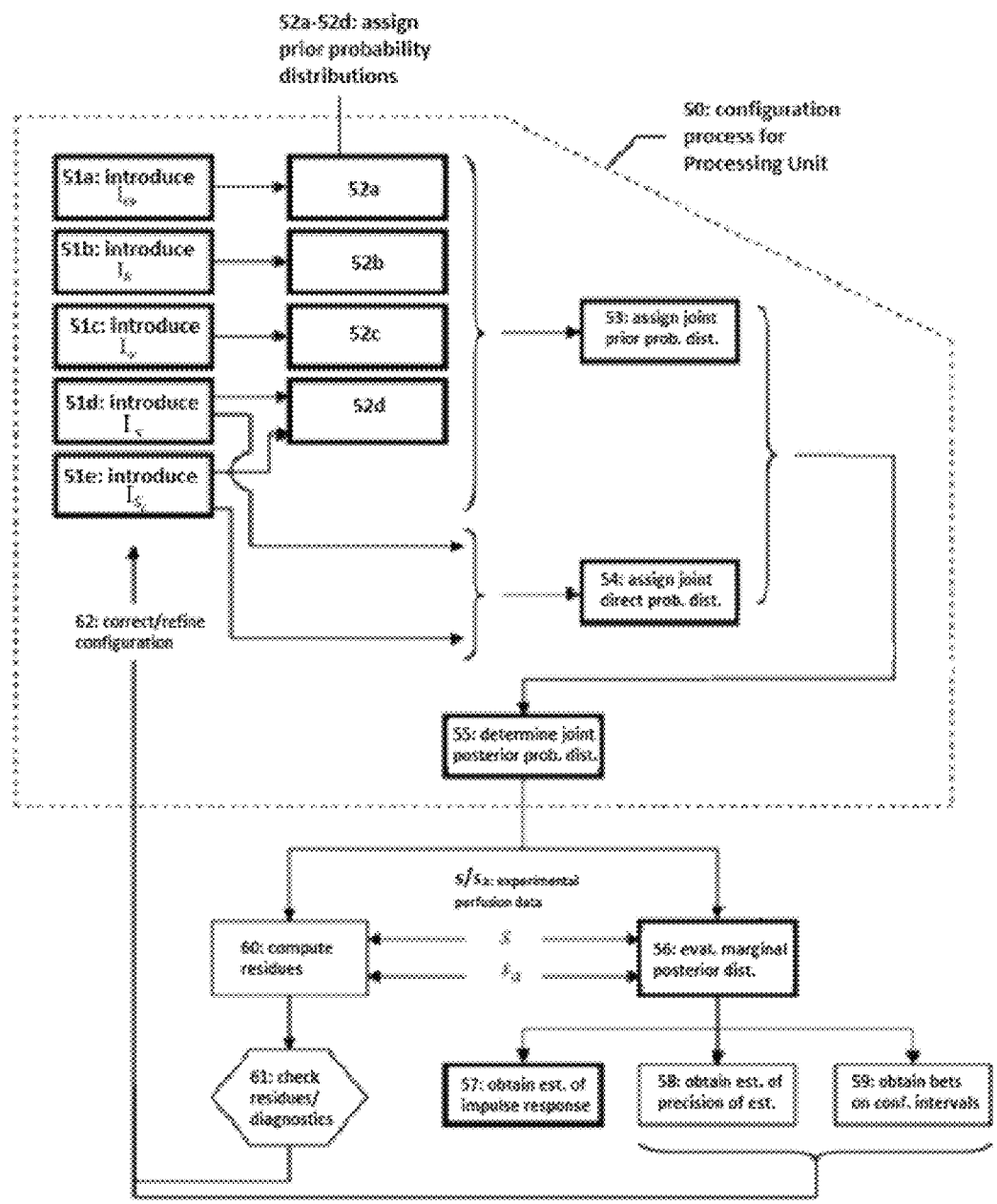
FIG. 8 shows a method according to the invention.

FIG. 8 shows an example of a method—according to the invention—for estimating a quantity of interest among a plurality of an artery/tissue/vein dynamical system of a voxel in an organ. Such a method can be carried out by a processing unit of a perfusion-weighted imaging analysis system as described in connection with FIGS. 1 and 2 and adapted accordingly.

A method according to the invention mainly comprises a step 56 for assigning one or several marginal posterior distributions for various quantities of interest to be estimated, such as hemodynamic parameters, the values of the theoretical impulse response at the sampling time points or the values of the complementary cumulative density function. It also includes a step 57 to compute said estimate.

To assign such a posterior marginal distribution, it is necessary to configure 50 the processing unit. The processing unit itself can preferably perform this configuration, by means of one or several configuration settings. The configuration can also yield the construction of a library of one or several marginal posterior distributions, said library being pre-established and stored in a program memory of said unit. The invention provides that said library can be enriched as it is used or delivered by an external processing unit capable of performing said configuration from said configuration settings and capable of cooperating with the processing unit for outputting said library.

A method according to the invention may thus comprise configuration steps carried out prior to the assignment 56, among which the following are necessary and sufficient:

the assignment 54 of the direct probability distribution for the experimental data given all the parameters involved in the problem of estimating the quantities of interest of the artery/tissue/vein dynamical system in the voxel in question;

the assignment 53 of the joint prior probability distribution for all those parameters.

The invention allows estimating one or several quantities of interest in various cases of application:

the theoretical arterial input functions are assumed to be known with absolute certainty and infinite accuracy;

the local arterial input functions differ from the global arterial input function by an unknown delay to be estimated as well;

the arterial input signal is only measured, possibly up to a delay;

the arterial input functions are not given and the arterial input signals are not measured—which is the most realistic case.

Configuration steps may depend on the case of application in question.

FIG. 8 illustrates a method according to the invention for a first example of application when the arterial input signal is measured, possibly up to a delay τ.

An experimental perfusion model M can be written as:

$$M : \begin{cases} s = \Psi(c, \Theta_S) + \xi \\ s_a = \Psi(a, \Theta_{S_a}) + \xi_a \\ c = BF \cdot Ab(t - \tau) = BF \cdot B(t - \tau)a \end{cases}$$

$b=[R(t_1), \ldots, R(t_N)]^T$ is a vector of the values of the unknown complementary cumulative density function. This vector may be expressed from the vector of the values of the impulse response $h=[h(t_1)=0, \ldots, h(t_N)]^T$. For instance, $$b = \left[1, 1, 1 - \Delta t \cdot h(t_2), \ldots, 1 - \Delta t \cdot \sum_{i=1}^{N-1} h(t_N)\right]^T$$

according to the left rectangle approximation method or $$b = \left[1, 1 - \Delta t \cdot h(t_2), \ldots, 1 - \Delta t \cdot \sum_{i=2}^{N} h(t_N)\right]^T$$

according to the right rectangle approximation method;

$c=[C(t_1), \ldots, C(t_N)]^T$ is a vector of the values of the unknown theoretical concentration of the contrast agent in the voxel;

$s=[S(t_1), \ldots, S(t_N)]^T$ is a real or complex vector of the experimental measures of the intensity signal by perfusion-weighted imaging;

$\Theta_S$ is a vector of the parameters linking $S(t)$ to $C(t)$;

$\xi=[\xi(t_1), \ldots, \xi(t_N)]^T$ is a vector of the measurement noises on said measured signal;

$s_a=[S_a(t_1), \ldots, S_a(t_N)]^T$ is a vector of the measurements of the experimental arterial input signal $S_a(t)$;

$\Theta_{S_a}$ is a vector of the parameters linking $S_a(t)$ to $C_a(t)$;

$\xi_a=[\xi_a(t_1), \ldots, \xi_a(t_N)]^T$ is a vector of the measurement noises on said arterial signal;

$a=[C_a(t_1), \ldots, C_a(t_N)]^T$ is a vector of the values of the unknown theoretical arterial input function $C_a(t)$;

A is a convolution matrix associated with the vector of the values of the unknown theoretical arterial input function a obtained by numerically approximating the convolution integral by the rectangle approximation method, the trapezoidal rule, or by higher-order methods such as Simpson's, Boole's, Gauss-Legendre's methods, etc. A may also be a circulant convolution matrix, such as those used in circular singular value decomposition method (cSVD).

We shall denote $\Theta$ the vector of the hemodynamic parameters of model M, for example here $\Theta=(BF,\tau)$.

In connection with FIGS. 1, 2 and 8, a method carried out by a processing unit 4 may comprise two initial configuration steps 51*d* et 51*e* consisting in introducing respectively information $I_S$ on the vector of the measures of the experimental signal s and information $I_{S_a}$ on the vector of the measures of the experimental arterial input signal $s_a$.

According to the invention, hard information is distinguished from soft information. A piece of hard information corresponds to any Boolean proposition regarded as certain—that is whose probability is equal to 1. For instance, Boolean propositions such as <<this curve is smooth>> or <<this signal follows this model>> constitute pieces of hard information. By contrast, a piece of soft information concerns any Boolean proposition that consists in indicating, and only indicating with a certain probability such Boolean propositions. At the end, this amounts to introducing Boolean propositions such as <<this curve is more or less smooth>> or <<this signal more or less follows this model>> . . . .

If we stick, for instance, to the first two moments $E(\xi,\xi_0)\equiv(0,0)$ and $E(\xi^2,\xi_a^2)=(\sigma_S,\sigma_{S_a})$ of the couple of the real-valued measurement noises vectors, then the Principle of Maximum Entropy (differential Shannon entropy under Lebesgue reference measure) requires that the vectors $\xi$ and $\xi_a$ must be regarded as mutually independent, white, stationary Gaussian stochastic processes with standard deviations $\sigma_S$ and $\sigma_S$ respectively.

More generally, we shall denote $(E_S, E_{S_a})$ the parameters characterizing the couple of the measurement noises vectors $(\xi, \xi_a)$. For example $(E_S, E_{S_a})=(\sigma_S, \sigma_{S_a})$.

A method according to the invention comprises a configuration step 54 for assigning a joint direct probability distribution for the couple of measurements vectors $(s, s_a)$ given the vectors a and b, the vector $\Theta$, the vectors of parameters $\Theta_S$ and $\Theta_{S_a}$ and the couple of the vectors $(E_S, E_{S_a})$. Said joint direct probability distribution then writes as $p(s,s_a|a,b,\Theta,\Theta_S,\Theta_{S_a},E_S,E_{S_a},I_S,I_{S_a},M)$.

For instance, we have:

$$p(s, s_a \mid a, b, \Theta, \Theta_S, \Theta_{S_a}, \sigma_S, \sigma_{S_a}, I_S, I_{S_a}, M) \propto (\sigma\sigma_a)^{-N} \exp$$

$$\left\{\sum_{i=1}^{N} \frac{[S(t_i) - \Psi(BF \cdot Ab(t_i - \tau), \Theta_S)]^2}{2\sigma^2} + \frac{[S_a(t_i) - \Psi(a(t_i), \Theta_{S_a})]^2}{2\sigma_a^2}\right\}$$

The invention can alternatively allows expressing the said joint direct probability distribution in a different way if we are interested, not directly in the vector b of the values of the unknown theoretical complementary cumulative density function, but in the vector h of the values of the impulse response. For this purpose, one should just express b in terms of h. Then, the joint direct probability distribution 54 writes for instance as $$p(s, s_a \mid a, h, \Theta, \Theta_S, \Theta_{S_a}, \sigma_S, \sigma_{S_a}, I_S, I_{S_a}, M) \propto (\sigma\sigma_a)^{-N} \exp$$

$$\left\{\sum_{i=1}^{N} \frac{[S(t_i) - \Psi(BF \cdot Ab(t_i - \tau), \Theta_S)]^2}{2\sigma^2} + \frac{[S_a(t_i) - \Psi(a(t_i), \Theta_{S_a})]^2}{2\sigma_a^2}\right\}$$

Without loss of generality, we shall consider afterwards, that one is preferentially interested in the vector h.

In the same way, one could further assign the joint direct probability distribution for the couple of the vectors of the measures of complex signals, by multiplying the direct probability distributions of their real and imaginary parts.

The invention also provides a variant when the vectors of the values of perfusion signals s and $s_a$ can be accurately converted into vectors of the values of the concentration $c_{exp}$, for instance by using $$c_{exp}(t_i) = -\frac{1}{k \cdot TE} \ln \frac{s(t_i)}{\mathbb{S}_0},$$

i=1,N in perfusion-weighted imaging by Nuclear Magnetic Resonance. It is possible to do so, for example, when the mean perfusion signal intensities $S_0$ before the arrival of the contrast agent can be estimated accurately and independently of other parameters. According to this embodiment, one can show that it is legitimate to assign a Gaussian probability distribution for the couple of vectors $(c_{exp}, c_{expa})$ given all other parameters such as:

$$p(c_{exp}, c_{expa} \mid a, h, \Theta, \sigma, \sigma_a, I_S, I_{S_a}, M) \propto$$

$$(\sigma\sigma_a)^{-N} \exp\left\{\sum_{i=1}^{N} \frac{[c_{exp}(t_i) - BF \cdot Ab(t_i)]^2}{2\sigma^2} + \frac{[c_{expa}(t_i) - a(t_i)]^2}{2\sigma_a^2}\right\}$$

$\sigma$ and $\sigma_a$ are now the standard deviations of the measurement noises on $c_{exp}$ and $c_{expa}$ respectively.

More generally, we shall use the terminology <<experimental perfusion data>> to designate a vector of the values of an experimental perfusion signal s as well as its conversion into a vector of the values of a concentration-time curve $c_{exp}$. Afterwards, we denote, without loss of generality, s and $s_a$ the experimental perfusion data.

Besides, the method comprises three configuration steps 51a, 51b et 51c that consist in introducing respectively a piece of information $I_\Theta$ on the hemodynamic parameters $\Theta$ of model M, a piece of information $I_h$ on the impulse response h and a piece of information $I_a$ on the arterial input function a. The pieces of information introduced at steps 51a to 51e constitute, according to the invention, configuration parameters for configuring—that is—making a processing unit capable of assigning 56 a posterior marginal distribution and, subsequently, of estimating 57 a quantity of interest. From those pieces of information—or configuration parameters—a method according to the invention may comprise a step 53 for assigning a joint prior probability distribution that can be written as $p(a,h,\Theta,\Theta_S,\Theta_{S_a},E_S,E_{S_a} \mid I_\Theta,I_h,I_a,I_S,I_{S_a},M)$.

Applying the Principle of Maximum Entropy, this distribution may typically factorize as:

$$p(a,h,\Theta,\Theta_S,\Theta_{S_a},E_S,E_{S_a} \mid I_\Theta I_h I_a I_S I_{S_a} M) = p(\Theta \mid I_\Theta,M) \cdot p(h,E_S \mid I_h,I_S,M) \cdot p(a,E_{S_a} \mid I_a,I_{S_a},M) \cdot p(\Theta_S,\Theta_{S_a} \mid I_S,I_{S_a},M)$$

Such a method thus comprises a step 52a that consists in assigning the prior probability distribution $p(\Theta \mid I_\Theta,M)$.

For example, one may assign a non-informative prior distribution. For instance, if information $I_\Theta$ consists only in knowing that BF and $\tau$ belong to the intervals $[BF_{min}, BF_{max}]$ and $[\tau_{min}, \tau_{max}]$ respectively, then the prior probability distribution $p(\Theta \mid I_\Theta,M)$ is a prior uniform Bayes-Laplace distribution:

$$p(\Theta \mid I_\Theta, M) = p(BF, \tau \mid I_\Theta, M) = \chi[BF_{min}, BF_{max}](BF) \cdot \chi[\tau_{min}, \tau_{max}](\tau) / [\log(BF_{max}) - \log(BF_{min})] / (\tau_{max} - \tau_{min}) BF$$

At the other end, one may also assign informative probability distributions such as relative frequency sampling distributions or marginal posterior probability distributions obtained from past experiments, for instance from quantitative perfusion-weighted imaging techniques such as Positron Emission Tomography (PET) or Arterial Spin Labeling (ASL).

A method according to the invention further comprises a configuration step 52b that consists in assigning the prior probability distribution $p(h,E_S \mid I_h,I_S,M) = p(h \mid I_S,I_h,M) \cdot p(E_S \mid I_S,M)$ from the piece of information $I_h$ (or $I_{\tilde{h}}$ if one is only interested in the complementary cumulative density function). This piece of information is made of pieces of hard and soft information.

For instance, regarding h(t), the pieces of hard quantitative information include $h(t_1) = h(0) = 0$ and for instance $$\int_0^{+\infty} h(t)dt \cong \Delta t \cdot \sum_{i=2}^{N} h(t_i) = 1$$

according to the right rectangle method. Both pieces of information allow reducing the number of values/parameters to be estimated to N−2. As we shall see, a judicious choice consists in keeping the values $h' = [h(t_2), \ldots, h(t_{N-1})]^T$ and expressing $h(t_N)$ by $$h(t_N) = 1/\Delta t - \sum_{i=2}^{N-1} h(t_i).$$

Besides, we can also consider the piece of hard quantitative information $\forall i=1,N \ h(t_i) \geq 0$. It thus remains to assign the joint prior probability distribution of vector h' by combining those pieces of hard quantitative information with a piece of purely qualitative and soft information. Let us consider for instance the piece of soft qualitative information $I_h^1$ « (t) is more or less smooth ». This qualitative information $I_h^1$ may first translate into the piece of soft quantitative information « the square of the second-order derivative of h is more or less large in average».

After time discretization at the sampling time points $t_i=1$, N, a second-order numerical approximation of the second-order derivative of h is given for instance by:

$$\forall i = 2, N-1, \quad \frac{d^2 h(t_i)}{dt^2} = \frac{h(t_{i-1}) + h(t_{i+1}) - 2h(t_i)}{\Delta t^2} + O(\Delta t^2)$$

One can also use higher-order numerical approximations, for instance the fourth-order formula:

$$\forall i = 3, N-2,$$

$$\frac{d^2 h(t_i)}{dt^2} = \frac{-\frac{1}{12}h(t_{i-2}) + \frac{4}{3}h(t_{i-1}) - \frac{5}{2}h(t_i) + \frac{4}{3}h(t_{i+1}) - \frac{1}{12}h(t_{i+2})}{\Delta t^2} + O(\Delta t^4)$$

Those numerical approximations can be written in matrix notations as $$\frac{d^2 h'}{dt^2} \simeq Dh$$

is for instance the square matrix $$D = \frac{1}{\Delta t^2}\begin{pmatrix} 0 & 0 & 0 & 0 & \ldots & \ldots & \ldots & 0 \\ 1 & -2 & 1 & 0 & \ddots & & & \vdots \\ 0 & 1 & -2 & 1 & 0 & \ddots & & \vdots \\ 0 & \ddots & \ddots & \ddots & \ddots & \ddots & \ddots & \vdots \\ \vdots & \ddots & \ddots & \ddots & \ddots & \ddots & \ddots & 0 \\ \vdots & & \ddots & 0 & 1 & -2 & 1 & 0 \\ \vdots & & & \ddots & 0 & 1 & -2 & 1 \\ 0 & \ldots & \ldots & \ldots & 0 & 0 & 0 & 0 \end{pmatrix}$$

of dimension N
in the case of the second-order approximation and h' is as defined above.

The square of the Euclidean norm of the second order-derivative of h' can thus be written as $$\left\|\frac{d^2 h'}{dt^2}\right\|^2 = (Dh)^T(Dh) = h^T(D^TD)h \equiv h^T W_1 h.$$

Qualitatively assuming the impulse response h(t) to be more ore less smooth may thus translate quantitatively by assuming $$\left\|\frac{d^2 h'}{dt^2}\right\| = \sqrt{h^T W_1 h}$$

to be more or less large. Hence, one seeks for the prior probability distribution p(h'|h(t$_1$),h(t$_N$),I)—the boundary points h(t$_1$) and h(t$_N$) being treated separately—among all the continuous probability distributions with same Euclidean norm $$\left\|\frac{d^2 h'}{dt^2}\right\|.$$

Following the Principle of Maximum Entropy—that consists in choosing among all those distributions with support the hyper-quadrant $[0,+\infty 00]^{N-2}$ the one having the highest differential Shannon Entropy (under Lebesgue reference measure) because it is the most uncertain and, subsequently, the most honest—one obtains the conditional multivariate truncated Gaussian distribution on $[0,+\infty]^{N-2}$ with constant vectorial mathematical expectation $M=(\mu_1, \ldots, \mu_1)^T$ and covariance matrix $$\frac{\varepsilon_1^2}{\sigma^2} W_1^{-1}$$

(or the multivariate Gaussian distribution truncated on $[0,1]^{N-2}$ for the vector of the values of the complementary cumulative density function):

$$p(h'|h(t_1), h(t_N), \mu_1, \varepsilon_1, E_S, I_h^1, M) =$$
$$C_1(\mu_1, \varepsilon_1, \sigma_S) \exp\left\{-\frac{\varepsilon_1^2(h-M)^T W_1(h-M)}{2\sigma_S^2}\right\}$$

where $C_1(\mu_1, \varepsilon_1, \sigma_S)$ is the normalization constant $$C_1(\mu_1, \varepsilon_1, \sigma_S) = \left[\int_{h' \in [0,+\infty]^{N-2}} \exp\left\{-\frac{\varepsilon_1^2(h-M)^T W_1(h-M)}{2\sigma_S^2}\right\} dh'\right]^{-1}$$

Hence, two new hyperparameters appear in our global perfusion model, the scalar mathematical expectation $\mu_1$ and the inverse fractional variance $\epsilon_1$ that plays the role of a regularization parameter for our perfusion model. $\epsilon_1$ quantifies the weight of the prior soft qualitative information $I_h^1$ with respect to the weight of the hard quantitative information provided by the experimental data s and s$_a$.

Besides, by definition:

$$p(h(t_1), h(t_N) | E_S, I_h^1, M) = p(h(t_1) | E_S, I_h^1, M) p(h(t_N) | E_S, I_h^1, M)$$
$$= \delta[h(t_1)] \cdot \delta\left[h(t_N) - 1/\Delta t \cdot \sum_{i=2}^{N-1} h(t_i)\right]$$

However, in order to take into account the fact that the delay r is almost never equal to a sampling time point t$_i$,i=1,N, we can let $$p(h(t_1) | \mu_{1,1}, \varepsilon_{1,1}, E_S, I_h^1, M) =$$
$$C_{1,1}(\mu_{1,1}, \varepsilon_{1,1}, \sigma_S) \exp\left\{-\frac{\varepsilon_{1,1}^2 [h(t_1) - \mu_{1,1}]^2}{2\sigma_S^2}\right\} h(t_1) \in [0, 1]$$

where $C_{1,1}(\mu_{1,1}, \varepsilon_{1,1}, \sigma_S)$ is the normalization constant $$C_{1,1}(\mu_{1,1}, \varepsilon_{1,1}, \sigma_S) = \left[\int_{h(t_1) \in [0,1]} \exp\left\{-\frac{\varepsilon_{1,1}^2 [h(t_1) - \mu_{1,1}]^2}{2\sigma_S^2}\right\} dh(t_1)\right]^{-1}$$

in order to indicate and only indicate that $h(\tau) \approx 0^+$.

Finally, the prior probability distribution for h of support the hyper-quadrant $[0,+\infty]^N$ for information $I_h^1$ can be written as:

$$p(h | \mu_1, \varepsilon_1, E_S, I_h^1, M) = \delta[h(t_1)] \delta\left[h(t_N) - 1/\Delta t + \sum_{i=2}^{N-1} h(t_i)\right]$$
$$C_1(\mu_1, \varepsilon_1, \sigma_S) \exp\left\{-\frac{\varepsilon_1^2(h-M)^T W_1(h-M)}{2\sigma_S^2}\right\}$$

Generally speaking, we shall denote $E_h$ (or $E_b$) the vector of the parameters of the prior distribution for h, for example $E_h = (\mu_1, \epsilon_1)$ or $E_h = (\mu_1, \epsilon_1, \mu_{1,1}, \epsilon_{1,1})$.

It remains to assign a prior probability distribution for $E_h$. One can typically assign for instance the non-informative improper Bayes-Laplace-Lhoste-Jeffreys distribution $p(\mu_1, \epsilon_1 | I_h^1, M) \propto \epsilon_1^{-1}$ or $p(\mu_1, \epsilon_1, \mu_{1,1}\epsilon_{1,1} | I_h^1, M) \propto \epsilon_1^{-1} \epsilon_{1,1}^{-1}$.

In the same way, on can introduce the piece of strictly soft quantitative information $I_h^2$ « the square of the first order derivative of h is more or less large in average».

One can finally obtains a new prior multivariate truncated Gaussian probability distribution for h by applying the Principle of Maximum Entropy.

It is worth noting that the pieces of soft information $I_h^1$, $I_h^2$, . . . as described before are the only pieces of information, the only constraints that can be legitimately introduced in our problem: they are not arbitrary hypotheses that can be verified or not by experiments but, on the contrary, they are just the expression of fundamental physiological properties without which the problem of estimating hemodynamic parameters, impulse responses or complementary cumulative density functions would be in fact absolutely meaningless: they are logically necessary and sufficient for our problem. Any other information would be on the contrary a simple hypothesis that can potentially be verified or falsified by experiments.

According to the invention, one may nevertheless introduce other pieces of soft information that are simple working hypothesis. For instance, one can indicate and only indicate that the impulse response more or less follows a given functional form without constraining it—by means of hard information—to exactly follow this form. Adding this kind of pieces of semi-quantitative soft information allows determining in what extent the impulse responses can be described by the proposed functional forms. Hence, let us assume for instance that one wants to introduce the piece of soft information—as mentioned above—$I_h^3$ « h(t) more or less follows a parametric or semi-parametric model $M_h$:f(t,$\Theta_h$) », $\Theta_h$ being the vector of the parameters of said model. As described before, such parametric models have been proposed, for instance the two-parameters $\Gamma$ model given by:

$$M_h: \begin{cases} f(t, \Theta_h) = t^{\frac{MTT}{\beta}-1} e^{-t/\beta} \Big/ \beta^{\frac{MTT}{\beta}} \Big/ \Gamma\!\left(\frac{MTT}{\beta}\right) MTT > 0, \beta > 0 \\ \Theta_h = (MTT, \beta) \\ \Gamma(): \text{fonction Gamma d'Euler} \end{cases}$$

Let us note that in this case, parameter MTT can be estimated directly, without having to numerically estimate the first moment of the impulse response (or the integral of the complementary cumulative density function) as described before.

Indicating that h more or less follows a given functional form f(t,$\Theta_h$) amounts to quantitatively indicating that the Euclidean norm of the residues $$\|h - f(t, \Theta_h)\|^2 = \sum_{i=1}^{N} [h(t_i) - f(t_i, \Theta_h)]^2$$

is more or less large. Applying again the Principle of Maximum Entropy, one finds in the same manner that the prior probability distribution for h is the multivariate Gaussian distribution truncated on the hyper-quadrant $$[0, +\infty]^N$$

$$p(h \mid E_h, E_S, \Theta_h, I_h^3, M_h, M) = $$

$$C_3(\varepsilon_3, \sigma_S, \Theta_h) \exp\!\left\{ -\frac{\varepsilon_3^2}{2\sigma_S^2} \sum_{i=1}^{N} [h(t_i) - f(t_i, \Theta_h)]^2 \right\}$$

where $C_3(\epsilon_3, \sigma_S, \Theta_h)$ is the normalization constant $$C_3(\varepsilon_3, \sigma_S, \Theta_h) = \left[ \int_{h \in [0,+\infty]^N} \exp\!\left\{ -\frac{\varepsilon_3}{2\sigma_S^2} \|h - f(t, \Theta_h)\|^2 \right\} dh \right]^{-1}.$$

In the same way, one may introduce a piece of soft information $I_h^4$ such as « h(t) more or less follows a given vector of values $\bar{h} = [\bar{h}(t_1), \ldots, \bar{h}(t_N)]^T$ ».

Applying the Principle of Maximum Entropy, one obtains the prior probability distribution:

$$p(h \mid E_h, E_S, I_h^4, M) \propto C_4(\varepsilon_4, \sigma_S, \bar{h}) \exp\!\left\{ -\frac{\varepsilon_4^2}{2\sigma_S^2} \sum_{i=1}^{N} [h(t_i) - \bar{h}(t_i)]^2 \right\}$$

where $C_4(\epsilon_4, \sigma, \bar{h})$ is the normalization constant $$C_4(\varepsilon_4, \sigma_S, \bar{h}) = \left[ \int_{h \in [0,+\infty]^N} \exp\!\left\{ -\frac{\varepsilon_4^2}{2\sigma_S^2} \|h - \bar{h}\|^2 \right\} dh \right]^{-1}.$$

The invention also allows combining several pieces of soft information on the impulse response h(t) (or the complementary cumulative density function) and their corresponding prior probability distributions. So, if $p(h|E_h^1, I_h^1, M), \ldots, p(h|E_h^n, I_h^n, M)$ are n prior probability distributions translating the pieces of information $I_h^n, \ldots, I_h^n$, with respective regularization parameters $E_h^1, \ldots, E_h^n$ (with for instance $E_h^1 = (\epsilon_1, \mu_1)$, $E_h^3 = (\epsilon_3, \Theta_h)$, etc.), then a prior distribution for h taking into account those n pieces of information may be written as $$p(h \mid E_h, I_h, M) = \prod_{k=1}^{n} p(h \mid E_h^k, I_h^k, M)$$

by denoting $E_h = (E_h^1, \ldots, E_h^n)$ and $I_h = I_h^1 \wedge \ldots \wedge I_h^n$.

In order to encode information $I_a$ on the local arterial input function, a method according to the invention further comprises a step 52c that consists in assigning a prior probability distribution $p(a, E_{S_a}|I_a, I_{S_a}, M) = p(a|E_{S_a}, I_a, M) \cdot p(E_{S_a}|I_{S_a}, M)$. Such a distribution is assigned in the same manner as the one related to the impulse response h, by introducing and combining pieces of hard and/or soft information on the arterial input function. For instance, one can specify that the arterial input function is more or less smooth, positive, unimodal, bimodal, zero at the origin, asymptotically zero, has a given area or indicate and only indicate that it more or less follows a given parametric or semi-parametric model $C_a(t, \Theta_a)$ where $\Theta_a$ is a vector of parameters, for instance the eleven-parameters « tri-Gamma » model:

$$M_a: \begin{cases} C_a(t, \Theta_a) = \dfrac{a(t - t_0)^{\alpha_0 - 1} e^{-(t - t_0)/\beta_0}}{\beta_0^{\alpha_0} \Gamma(\alpha_0)} + \\ \quad \dfrac{b(t - t_1)^{\alpha_1 - 1} e^{-(t - t_1)/\beta_1}}{\beta_1^{\alpha_1} \Gamma(\alpha_1)} + \dfrac{(1 - a - b)(t - t_2)^{\alpha_2 - 1} e^{-(t - t_2)/\beta_2}}{\beta_2^{\alpha_2} \Gamma(\alpha_2)} \\ \Theta_a = (a, b, \alpha_0, \beta_0, t_0, \alpha_1, \beta_1, t_1, \alpha_2, \beta_2, t_2) \\ \Gamma(): \text{fonction Gamma d'Euler} \end{cases}$$

As described before, one obtains a Gaussian prior probability distribution $$p(a \mid E_a^1, E_{S_a}, \Theta_a, I_a^1, M_a, M) =$$

$$C(\varepsilon_a^1, \sigma_{S_a}, \Theta_a) \exp\!\left\{ -\frac{(\varepsilon_a^1)^2}{2\sigma_{S_a}^2} \sum_{i=1}^{N} [a(t_i) - C_a(t_i, \Theta_a)]^2 \right\}$$

where $C(\epsilon_a^1, \sigma_{S_a}, \Theta_a)$ is the normalization constant $$C(\varepsilon_a^1, \sigma_{S_a}, \Theta_a) = \left[ \int_{a \in [0,+\infty]^N} \exp\!\left\{ -\frac{(\varepsilon_a^1)^2 \|a - C_a(t, \Theta_a)\|^2}{2\sigma_{S_a}^2} \right\} da \right]^{-1}.$$

As well, it is possible to indicate and only indicate (otherwise we come back to the case where the arterial input function is given) that the vector a is more or less close to a given vector of values $\bar{a}=[\bar{a}(t_1), \ldots, \bar{a}(t_N)]^T$ such as a local arterial input function: one gets the prior probability distribution $$p(a \mid E_a^2, E_{S_a}, I_a^2, M) = C_a(\varepsilon_a^2, \sigma_{S_a}, \bar{a}) \exp\left\{-\frac{(\varepsilon_a^2)^2}{2\sigma_{S_a}^2} \sum_{i=1}^N [a(t_i) - \bar{a}(t_i)]^2\right\}$$

where $C(\epsilon_a, \sigma_a, \bar{a})$ is the normalization constant $$C_a(\varepsilon_a^2, \sigma_{S_a}, \bar{a}) = \left[\int_{a \in [0, +\infty]^N} \exp\left\{-\frac{(\varepsilon_a^2)^2 \|a - \bar{a}\|^2}{2\sigma_{S_a}^2}\right\} da\right]^{-1}.$$

A method according to the invention further comprises a configuration step 52d that consists in assigning a prior probability distribution $p(E_S, E_{S_a}, \Theta_S, \Theta_{S_a} | I_S, I_{S_a}, M)$ that typically factorizes as:

$$p(E_S, E_{S_a}, \Theta_S, \Theta_{S_a} | I_S, I_{S_a}, M) = p(E_S | I_S, M) \cdot p(E_{S_a} | I_{S_a}, M) \cdot p(\Theta_S | I_S, M) \cdot p(\Theta_{S_a} | I_{S_a}, M)$$

For instance, we have the non-informative prior probability distribution:

$$p(E_S, E_{S_a}, \Theta_S, \Theta_{S_a} | I_S, I_{S_a}, M) = p(\sigma_S | I_S, M) \cdot p(\sigma_{S_a} | I_{S_a}, M) \cdot$$
$$p(S_0 | I_S, M) \cdot p(S_{0_a} | I_{S_a}, M)$$
$$= (\sigma_S \cdot \sigma_{S_a})^{-1} / (S_0^{max} - S_0^{min}) / (S_{0_a}^{max} - S_{0_a}^{min})$$

Taking into account the different hyperparameters introduced in steps 52b to 52d, the joint prior probability distribution 53 can be rewritten as $p(a, E_a, h, E_h, \Theta, \Theta_S, \Theta_{S_a}, E_S, E_{S_a} | I_\Theta, I_h, I_a, I_S, I_{S_a}, M)$.

In order to simplify the following expressions, we denote $I=(I_\Theta, I_h, I_a, I_S, I_{S_a}, M)$ the set of the pieces of information entered as configuration parameters of the processing unit.

Given a direct probability distribution 54 and a joint prior probability distribution 53 as described before, we get the joint posterior probability distribution 55 for all parameters by applying Bayes rule:

$$p(a, E_S, h, E_h, \Theta, \Theta_S, \Theta_{S_a} E_S, E_{S_a} | s, s_a, I) =$$
$$\frac{p(a, E_a, h, E_h, \Theta, \Theta_S, \Theta_{S_a}, E_S, E_{S_a} | I) \cdot}{p(s, s_a | I)} \propto$$
$$p(s, s_a | a, h, \Theta, \Theta_S, \Theta_{S_a} E_S, E_{S_a}, I)$$
$$p(a, E_a, h, E_h, \Theta, \Theta_S, \Theta_{S_a}, E_S, E_{S_a} | I) \cdot$$
$$p(s, s_a | a, h, \Theta, \Theta_S, \Theta_{S_a}, E_S, E_{S_a}, I)$$

The initial configuration being done, the invention now allows estimating a quantity of interest that we shall denote $\theta$ among all the elements of the vector $\Xi=(a, E_a, h, E_h, \Theta, \Theta_S, \Theta_{S_a}, E_S, E_{S_a})$. For instance, $\theta=BF$ or $\theta=\tau$, or $\theta=h(t_i)$, etc.

A method according to the invention thus comprises a step 56 that consists in evaluating the marginal posterior distribution for $\theta$, that is $$p(\theta | s, s_a, I) = \int_{\Xi \setminus \theta} p(\Xi | s, s_a, I) d(\Xi \setminus \theta).$$

From this marginal posterior distribution, one can obtain 57 estimates $\hat{\theta}$ of $\theta$. For example, one obtains the Bayes estimator under the quadratic loss function $L(\theta - \hat{\theta}^Q) = \|\theta - \hat{\theta}^Q\|^2$ where $\| \|$ is the Euclidean norm by taking the mathematical expectation of this distribution $$\hat{\theta}^Q = \int_\theta \theta \cdot p(\theta | s, s_a, I) d\theta.$$

In the same way, one can obtain the maximum a posteriori estimator $\hat{\theta}^P$—MAP—by $$\hat{\theta}^P = \underset{\theta}{\operatorname{argmax}} p(\theta | s, s_a, I).$$

As an example, one can obtain the marginal posterior probability distribution of the value $h(t_i), i=1, N$ of the impulse response at each sampling time point $t_i$, by marginalizing all other time points:

$$\forall i = 1, N,$$

$$p(h(t_i) | s, s_a, I) = \int_{\substack{h(t_j) \\ j \neq i}} p(h | s, s_a, I) dh(t_1) \ldots dh(t_{j \neq i}) \ldots dh(t_N)$$

and, subsequently, obtain estimates of those values such as $\hat{h}^Q(t_i)$ or $\hat{h}^P(t_i)$.

In the same way, it is also possible to obtain 57 an estimate $\hat{h}(x)$ (or $\hat{R}(x)$) of the value of the impulse response $h(x)$ at any time point $x$, not necessarily equal to a sampling time point $t_i$. For this purpose, it is sufficient to introduce $h(x)$ in the expression of the values of the complementary cumulative density function $R(t)$ as described before and to compute its marginal probability distribution. It is even desirable to introduce such additional time points $x_1 \ldots, x_L$ in the estimation problem since the larger the number of time points taken into account the better the numerical approximations of integrals such as $$\int_0^t h(\tau) d\tau \int_0^{+\infty} h(\tau) d\tau = 1 \int_0^t C_a(\tau) \cdot \left[H(t-\tau) - \int_0^{t-\tau} h(v) dv\right] d\tau$$

as well as the numerical approximations of $$\frac{d^2 h}{dt^2} \text{ or } \frac{dh}{dt}.$$

Subsequently, the resulting estimates are also better.

Then, since $$MTT = Eh = \int_0^{+\infty} t \cdot h(t) dt,$$

one can obtain estimates of this parameter such as the <<mean>> estimate $$\widehat{MTT}^Q = \Delta t \cdot \sum_{i=2}^{N} t_i \cdot \hat{h}^O(t_i)$$

the most probable estimate $$\widehat{MTT}^P = \Delta t \cdot \sum_{i=2}^{N} t_i \cdot \hat{h}^P(t_i)$$

by applying a numerical integration method, for instance here the right rectangle method.

Moreover, a method according to the invention may comprise a step 58 for obtaining an estimate of the precision on the estimate of parameter θ, and even confidence intervals on those estimates. The invention provides that such a method may further comprise a step 59 for obtaining bets on said confidence intervals. For example, the precision on the estimate $\hat{\theta}^Q$ may be quantified by the covariance matrix of the marginal posterior probability distribution for θ:

$$\hat{\sigma}\hat{\theta}^{Q^2} = \int_\theta (\theta - \hat{\theta}^Q)(\theta - \hat{\theta}^Q)^T p(\theta|s, s_a, I) d\theta$$

Then we have for instance a confidence (hyper-) interval at <<one sigma>> for θ J=[$\hat{\theta}^Q$−diag($\hat{\sigma}\hat{\theta}^Q$),$\hat{\theta}^Q$+diag($\hat{\sigma}\hat{\theta}^Q$)] and the probability that θ belongs to this interval $$p_J = \int_{\theta \in J} p(\theta|s, s_a, I) d\theta \text{ or,}$$

equivalently, the betting odds $$\frac{p_J}{1 - p_J}.$$

It also possible to obtain estimates, confidence intervals, and bets on those confidence intervals for the parameter BV=BF·MTT, the vector of the value of the complementary cumulative density function b, the vector of the values of the venous output function v=Ah or the vector c=BF.Ab of the values of the theoretical concentration-time curve because, given the joint probability distribution of several random variables, one can compute the probability density function of an arbitrary function of them. For example, by linearity of the mathematical expectation, we immediately obtain the estimates of the values of the complementary cumulative density function R(t) from those of the impulse response $$\hat{b}^Q = \left(1, 1 - \Delta t \cdot \hat{h}^O(t_2), \ldots, 1 - \Delta t \cdot \sum_{i=2}^{N} \hat{h}^O(t_N)\right)^T \text{ and}$$

$$\hat{b}^P = \left(1, 1 - \Delta t \cdot \hat{h}^P(t_2), \ldots, 1 - \Delta t \cdot \sum_{i=2}^{N} \hat{h}^P(t_N)\right)^T$$

by following for instance the right rectangle method. In the same way, from the joint probability distribution p(c,Θ$_S$|s,s$_a$,I) for c and Θ$_S$, one can also derive the probability distribution $s_{th}$=[$S_{th}$(t$_1$), ..., $S_{th}$(t$_N$)]$^T$ of the values of the theoretical perfusion signal $S_{th}$(t) since $s_{th}$=Ψ(c,Θ$_S$).

From this distribution, one can obtain 57 estimates $\widehat{s_{th}}$ as well as confidence hyper-intervals 58 and bets 59 on those hyper-intervals following a method similar to that described above.

The invention provides that the confidence intervals or the bets on said confidence intervals, may allow setting 62 the configuration of the processing unit. So, it is possible to modify the configuration parameters and to provide higher quality estimates.

The invention further provides that a method may comprise a step 60 for computing the residues r(t$_i$)=S(t$_i$)−$\widehat{s_{th}}$(t$_i$),i=1,N between theoretical and experimental perfusion-weighted signals. The invention then allows computing various statistics or distances D(s,$\widehat{s_{th}}$) between those vectors, the most classical one being the sum of $$\text{squared errors} - SSE - \chi^2 = \sum_{i=1}^{N} r(t_i)^2.$$

Those various statistics allow quantifying the goodness-of-fit of the perfusion model to experimental data. In this way, one obtains <<error maps>> for the model in each voxel of interest. For the reasons mentioned above (i.e. the overfitting issue), the quantification of the goodness-of-fit of the perfusion model to experimental data s and s$_a$ may be particularly advantageously achieved by computing the probability of the experimental data (s,s$_a$) given the perfusion model in each voxel of interest:

$$p(s, s_a | I) = \int_\Xi p(s, s_a | \Xi, I) p(\Xi|I) d\Xi$$

In this case, the error map would be based on 1−p(s,s$_a$|I).

The invention also provides that one may apply 61 various statistical tests or various graphical diagnosis techniques such as Q-Q plots or Poincaré's return maps in order to check if the residues r(t$_i$) are actually independent, identically distributed and Gaussian, etc. The invention thus provides that, by an iterative process and trial and error, one can correct and refine 62 the configuration process 50, in particular the theoretical perfusion models in order to make progress in the modeling, the understanding and the processing of perfusion phenomena and to obtain in fine better estimates of hemodynamic parameters, impulse responses, complementary cumulative density functions, arterial input functions or venous output functions.

In connection with FIG. 8, let us now describe a method according to the invention for a second example of application for which the theoretical arterial input functions are assumed to be given with absolute certainty and infinite accuracy up to a delay r.

Then, an experimental perfusion model M may write as:

$$M: \begin{cases} s = \Psi(c, \Theta_S) + \xi \\ c = BF \cdot Ab(t - \tau) = BF \cdot B(t - \tau)a \end{cases}$$

where all quantities are as defined before except $a=[C_a(t_1), \ldots, C_a(t_N)]^T$ that is the vector of the values of the theoretical arterial input function now assumed to be known.

The joint direct probability distribution thus writes as $p(s|a,h,\Theta,\Theta_S,E_S,I)$ and the joint prior probability distribution as $p(h,E_h,\Theta,\Theta_S,E_S|I)$ with $I=(I_\Theta,I_h,I_S,M)$. Those distributions are assigned as described before. Bayes rule becomes $$p(h,E_h,\Theta,\Theta_S,E_S|s,a,I) \propto cp(h,E_h,\Theta,\Theta_S,E_S|a,I) \cdot p(s|a,h,\Theta,\Theta_S,E_S,I)$$

One subsequently obtains estimates, confidence intervals and bets on those confidence intervals for any parameter $\theta \in \Xi=(h,E_h,\Theta,\Theta_S,E_S)$ in the same manner as previously described.

In connection with FIG. 8, let us now describe a method according to the invention for a third example of application for which the theoretical arterial input functions are not given and the arterial input signals are not measured.

Then, an experimental perfusion model M may write as:

$$M: \begin{cases} s = \Psi(c, \Theta_S) + \xi \\ c = BF \cdot Ab(t) = BF \cdot B(t)a \end{cases}$$

where all quantities are as defined before.

The joint direct probability distribution still writes as $p(s|a,h,\Theta,\Theta_S,E_S,I)$ and the joint prior probability distribution now writes as $p(a,E_a,h,E_h,\Theta,\Theta_S,E_S|I)$ with $I=(I_0,I_h,I_a,I_S,M)$. Bayes rule becomes $p(a,E_a,h,E_h,\Theta,\Theta_S,E_S|s,I) \propto p(a,E_a,h,E_h,\Theta,\Theta_S,E_S|I) \cdot p(s|a,h,\Theta,\Theta_S,E_S,I)$ One subsequently obtains estimates, confidence intervals and bets on those confidence intervals for any parameter $\theta \in \Xi=(a,E_a,h,E_h,\Theta,\Theta_S,E_S)$ in the same manner as previously described.

It is worth noting that, whatever the example of application in question, contrary to known methods, an estimation method according to the invention is an exact method, in that it consists and only consists in translating pieces of qualitative, quantitative or semi-quantitative information that we have a priori on the quantities of interest into Bayesian Probability Theory in order to univocally determine the posterior information on those quantities provided by the experimental measurements. No arbitrary hypothesis that could be verified or not—in particular on the impulse responses or on the complementary cumulative density functions—is necessary because the invention only introduces the most uncertain probability distributions encoding the various soft qualitative constraints that are logically necessary and sufficient in order to solve the problem.

It follows that, when the arterial input functions are not assumed to be given but at most measured, those methods allow testing if the proposed arterial input signals can effectively correspond to true local arterial input functions for each voxel of interest: indeed, if the arterial input signals are not suitable and do not correspond to the true local arterial input functions, it may be that there is no set of parameters (hemodynamic parameters, complementary cumulative density functions, etc.) that is a solution of the problem while fulfilling at the same time the various prior constraints (or at least whose probability is not negligible a priori). In this case, Probability Theory shall interpret the proposed arterial input signals as noise: the standard deviations $\sigma_a/\epsilon_a$ shall be much larger compared to those typically obtained from more suitable arterial input signals.

The invention thus has a particularly interesting application to test different selection and estimation methods of global or local arterial input functions according to the state-of-the-art. If it turns out that the estimates, in particular those on their regularization parameters $E_a$, obtained from those global or local arterial input functions are too often aberrant from one voxel to the other, one shall conclude that it is necessary either to introduce new, more suitable (local) selection methods of those functions or to resort to methods that do not require the arterial input functions to be given or arterial input signals to be previously measured, which is precisely the purpose of the third method described above.

As an example of application, we can mention the main implementation steps of the invention by a perfusion-weighted analysis imaging system, as described in FIGS. 1 or 2:

opening of a patient record or importation of images sequences by a processing unit 4 (or a preprocessing unit 7) in order to select the images sequences of interest—in particular, selection of perfusion-weighted images I1 to In over time from which perfusion signals are obtained S(t) for each voxel, as illustrated by FIG. 5a;

preview by means of a human-machine interface 5 of images in order to allow a user 6 identifying slices or regions of interest;

configuration of processing unit 4 from configuration parameters (input pieces of information) in order to allow implementing the estimation method according to the invention;

selection of the quantity or the quantities of interest to be estimated;

estimation by the processing unit 4 of hemodynamic parameters 14, such as $\widehat{BF}, \hat{\tau}$ or $\widehat{MTT}$, for organ such as the human brain;

optional estimation of other parameters such as $E_h$, $E_S$, $\Theta_S$ or $E_a$, $E_{S_a}$ or $\Theta_{S_a}$ when the arterial input function is not given;

optional estimation of vectors of the values of the impulse responses $\hat{h}$, the complementary cumulative density functions $\hat{b}$, vectors of the values of the arterial input function $\hat{a}$, vectors of the values of the venous output functions $\hat{v}$, vectors of the values of the theoretical concentrations $\hat{c}$, theoretical signals $\widehat{s_{th}}$ or residues $\hat{r}$;

release of said estimated quantities of interest 14 to the human-machine interface 5 so that it finally displays them for instance as maps where the intensity or the color of each pixel depends on the calculated value in order to render their content to the medical practitioner;

optional display of the estimates of impulse responses, complementary cumulative density functions, arterial input functions, venous output functions, theoretical concentrations, theoretical signals or residues for some voxels of interest selected by the user;

optional display of confidence maps or bets maps for one or several parameters of interest such as the hemodynamic parameters;

optional display of confidence intervals or bets on those intervals for some impulse responses, complementary cumulative density functions, arterial input functions, etc. for some voxels of interest selected by the user;

optional display of error maps for one or several distanced between experimental data and a global nonparametric perfusion model, in particular display of the probability of the experimental data given the global perfusion model;

aided selection of said pathological region of interest, characterized by an abnormal distribution of one or several hemodynamic parameters, of the impulse responses (or the complementary cumulative density functions) or of the local arterial input functions;

estimation, by the processing unit, of the volume of the abnormally perfusion tissue region possibly related to a lesion region and for which the medical practitioner may decide on a therapeutic action (intravenous thrombolysis in order to breakdown the blood clot for instance);

estimation, by the processing unit, of some quantities, such as the ratio between the volumes of the lesion and the abnormally perfused regions for which a medical practitioner may refine its diagnosis and therapeutic decision (intravenous thrombolysis in order to breakdown the blood clot for instance);

As described before, the configuration process 50 of processing unit 4 may be performed by the unit itself (execution of process 50). Alternatively, said configuration may consist in storing and selecting a library of joint posterior probability distributions depending on the quantities of interest that one wants to estimate. The construction of this library may be achieved by means of a dedicated unit capable of cooperating with processing unit 4.

Alternatively, iterations may occur following the estimation of confidence intervals, bets on those confidence intervals for some quantities of interest in order to refine said configuration. The provision of distances between experimental data and a global nonparametric perfusion model, in particular the display of the probability of the experimental data given the global perfusion model may also induce an update of the configuration.

The invention thus aims to display parameter estimates in the form of <<parameter maps>> where the intensity or the color of each voxel depends on the calculated value, for instance in a linear way. As well, the invention possibly aims to display the standard deviation of those estimates in the form of <<confidence maps>> as well as bets on the corresponding confidence intervals in the form of <<bets maps>>. Regarding the estimates of the vectors of the values of impulse responses, complementary cumulative density functions, arterial input functions, the venous output functions, concentration-time curves, perfusion signals or residues, the invention aims to display them in the form of time series for each voxel selected by the user. Last, the invention aims to display distances between experimental signals and a nonparametric perfusion model or the probability of the experimental data given this model in the form of <<error maps>>.

FIGS. 9 á 12 allow illustrating a display mode in the form of maps of some quantities of interest such as the hemodynamic parameters 14 estimated according to the invention or even standard deviations or probabilities associated with them.

So, for a human brain analyzed by means of Nuclear Magnetic Resonance Imaging, FIG. 9 allows viewing an estimate of cerebral blood volumes CBV. Such a map (458×458 pixels) allows highlighting a probable ischemic region 80. Indeed, one can observe by means of a suitable interface 6, a clear increase of parameter CBV in the territory of the right posterior cerebral artery compared to the contralateral hemisphere. A vasodilatation subsequent to the ischemia reveals itself by reading the map illustrated by FIG. 9.

FIG. 10 allows illustrating a map (458×458 pixels) related to the estimation of cerebral blood flows in an ischemic stroke case. One can observe by analyzing the map a decrease of parameter CBF (Cerebral Blood Volumes) in the territory of the right posterior cerebral artery compared to the contralateral hemisphere subsequent to the ischemia. Such a map allows highlighting a probable ischemic region 80.

FIG. 11 allows illustrating a map (458×458 pixels) related to the estimation of the mean transit times MTT. One can observe by analyzing the map a clear increase of MTT in the territory 81 of the right posterior cerebral artery compared to the contralateral hemisphere subsequent to the ischemia.

FIG. 12 allows describing a map (458×458 pixels) related to the estimation of the probability that the cerebral blood flow belongs to the confidence interval [$\widehat{CBF} - \hat{\sigma}CBF$, $\widehat{CBF} + \hat{\sigma}CBF$]. By analyzing the map, one can observe that, except aberrant model fits, the probabilities are centered around 0.68. This is a value that one is entitled to expect if the posterior probability distribution for CBF follows a Gaussian law.

Thanks to the maps described before, the invention enables to provide a user a variety of useful information, information that could not be available using techniques known to the state-of-the-art. This provision is made possible by adapting the processing unit 4 as described in FIG. 1 or 2 in that its means for communicating with the external world are capable of delivering estimated parameters 14 in a format suitable for a human-machine interface 5 capable of rendering to a user 6 said estimated parameters in the form, for instance, of maps as illustrated by FIGS. 9 to 13.

Thanks to the invention, the pieces of information that are provided are more numerous and fairer. The information available to the medical practitioner is likely to increase the confidence of the medical practitioner's in his determination of a diagnostic and his therapeutic decision-making.

In order to improve the performances of the system according to the invention, it provides that the processing unit may comprise means for parallelizing the calculations over the image voxels for which the estimation of hemodynamic parameters, complementary cumulative density functions or arterial input functions are required. This may be achieved by using hardware technologies such as Graphical Processor Units (GPU) computer clusters or software technologies such as parallel Monte-Carlo methods, etc. Alternatively, the processing unit according to the invention may rely on remote computational means. In this way, computation times can be further reduced significantly.

The invention claimed is:

1. A method for estimating a quantity of interest, among a plurality of quantities of interest of an artery/tissue/vein dynamical system, in an elementary volume of an organ, wherein the elementary volume is referred to as a voxel, said method being carried out by a processing unit of a perfusion weighted imaging analysis system, and comprising a step for estimating said quantity of interest from experimental perfusion data, wherein said step comprises evaluating—according to a Bayesian method—a posterior marginal probability distribution for said quantity of interest by:

assigning a direct probability distribution for the experimental perfusion data given parameters involved in the estimation of the quantities of interest of the artery/tissue/vein dynamical system in said voxel; and assigning a joint prior probability distribution for said quantities, by introducing purely soft information on an impulse response of said dynamical system and applying the Principle of Maximum Entropy.

2. A method for estimating a quantity of interest, among a plurality of quantities of interest of an artery/tissue/vein dynamical system, in an elementary volume of an organ, wherein the elementary volume is referred to as a voxel, said dynamical system being (i) linear, (ii) time-invariant and (iii) formally determined by the relationship $C(t) = BF \cdot C_a(t) \otimes R(t)$, where C(t) is a concentration of a contrast agent circulating in a voxel, $C_a(t)$ is a concentration of said contrast agent in an artery feeding said voxel, BF is a blood flow in said voxel, ⊗ stands for a convolution product and R(t) is a complementary cumulative density function of a transit time of said contrast agent in said voxel, said method being carried out by a processing unit of a perfusion weighted imaging analysis system, and comprising a step for estimating said quantity of interest from experimental perfusion data, wherein said step comprises evaluating—according to a Bayesian method—a posterior marginal probability distribution for said quantity of interest by:

assigning a direct probability distribution for the experimental perfusion data given parameters involved in the estimation of the quantities of interest of the artery/tissue/vein dynamical system in said voxel; and assigning a joint prior probability distribution for said quantities, by introducing purely soft information on the complementary cumulative density function R(t) in said voxel and applying the Principle of Maximum Entropy.

3. A method according to claim 1, wherein the assignment of a joint prior probability distribution for said quantities is further achieved by introducing purely soft information on a concentration-time curve of said contrast agent in an artery feeding the voxel and applying the Principle of Maximum Entropy.

4. A method according to claim 1, wherein the method is executed by successive iterations for a plurality of voxels in question.

5. A method according to claim 1, further comprising a step for computing supplementary information represented by a confidence interval associated with an estimated quantity of interest.

6. A method according to claim 1, further comprising a step for computing supplementary information represented by a bet on a confidence interval associated with an estimated quantity of interest.

7. A method according to claim 4, further comprising a step for computing supplementary information represented by a measure of an adequacy of the product of:

the assignment of the direct probability distribution for the experimental perfusion data given the parameters involved in estimating the quantities of interest of the artery/tissue/vein dynamical system in the voxel in question; and the assignment of the joint prior probability distribution for said quantities.

8. A method according to claim 5, further comprising a step for delivering an estimated quantity of interest to a human-machine interface capable of rendering the estimated quantity to a user.

9. A method according to claim 5, further comprising a step for delivering supplementary information associated with said estimated quantity of interest to a human-machine interface capable of rendering the supplementary information to a user.

10. A method according to claim 1, wherein the experimental perfusion data comprises a vector of values of an experimental perfusion signal or a conversion of said vector of values into a vector of values of a concentration-time curve.

11. A processing unit comprising means for storing, means for communicating with external devices, and means for processing, wherein:

the means for communicating are capable of receiving experimental perfusion data external devices world; and the means for processing is configured to execute a method for estimating a quantity of interest among a plurality of quantities of interest of an artery/tissue/vein dynamical system in an elementary volume of an organ, wherein the elementary volume is referred to as a voxel, according to the method of claim 1.

12. A processing unit according to claim 11, wherein the means for communicating are capable of delivering an estimated quantity of interest in a format suitable for a human-machine interface capable of rendering the estimated quantity to a user.

13. A processing unit according to claim 12, wherein the means for communicating are capable of delivering supplementary information associated with an estimated quantity of interest in a format suitable for a human-machine interface capable of rendering the supplementary information to a user.

14. A perfusion weighted imaging analysis system comprising a processing unit according to claim 11 for estimating a quantity of interest, and a human-machine interface capable of rendering the estimated quantity to a user.

* * * * *